US009770418B2

(12) United States Patent
Rahimipour et al.

(10) Patent No.: US 9,770,418 B2
(45) Date of Patent: Sep. 26, 2017

(54) DOPAMINE NANOCAPSULES AND USES THEREOF

(71) Applicant: BAR-ILAN UNIVERSITY, Ramat Gan (IL)

(72) Inventors: Shai Rahimipour, Rehovot (IL); Gil Yeroslavsky, Tel Aviv (IL); Michal Richman, Kfar-Saba (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 312 days.

(21) Appl. No.: 14/149,704

(22) Filed: Jan. 7, 2014

(65) Prior Publication Data

US 2014/0193489 A1 Jul. 10, 2014

Related U.S. Application Data

(60) Provisional application No. 61/749,397, filed on Jan. 7, 2013.

(51) Int. Cl.
| *A61J 3/07* | (2006.01) |
| *A61K 47/48* | (2006.01) |
| *A61K 9/48* | (2006.01) |
| *A61K 33/24* | (2006.01) |
| *A01N 25/28* | (2006.01) |
| *A61K 9/50* | (2006.01) |
| *A61K 9/51* | (2006.01) |

(52) U.S. Cl.
CPC ............ *A61K 9/4816* (2013.01); *A01N 25/28* (2013.01); *A61K 47/48869* (2013.01); *A61K 9/5094* (2013.01); *A61K 9/5138* (2013.01)

(58) Field of Classification Search
CPC ........ A01N 25/28; A01N 59/16; A01N 59/20; A61K 47/48869; A61K 9/4816; A61K 9/5094; A61K 9/5138
See application file for complete search history.

(56) References Cited

U.S. PATENT DOCUMENTS

2014/0336040 A1* 11/2014 Yan .................... C08G 73/0688
502/159

OTHER PUBLICATIONS

Cui et al. (Adv. Funct. Mater. 2010, 20 1625-1631.*
Zhang et al. (Green Chem., 2011, 13, 300-306).*
Asati, A., Santra, S., Kaittanis, C., Nath, S., Perez, J.M., "Oxidase Activity of Polymer-Coated Cerium Oxide Nanoparticles" Angewandte Chemie International Edition vol. 48, pp. 2308-2312 (2009).
Avivi, S., Gedanken, A., "S—S bonds are not required for the sonochemical formation of proteinaceous microspheres: the case of streptavidin" Biochemical Journal 366 pp. 705-707 (2002).
Cui, J.W., Wang, Y.J., Postma, A., Hao, J.C., Hosta-Rigau, L., Caruso, F., "Monodisperse Polymer Capsules: Tailoring Size, Shell Thickness, and Hydrophobic Cargo Loading via Emulsion Templating" Advanced Functional Materials 20, pp. 1625-1631 (2010).
Cui, J., Yan, Y., Such, G.K., Liang, K., Ochs, C.J., Postma, A., Caruso, F., "Immobilization and Intracellular Delivery of an Anticancer Drug Using Mussel-Inspired Polydopamine Capsules" Biomacromolecules, 13, pp. 2225-2228 (2012).
Del Duca, M., Yeager, E., Davies, M.O., Hovorka, F., "Isotopic Techniques in the Study of the Sonochemical Formation of Hydrogen Peroxide" The Journal of the Acoustical Society of America, 30, pp. 301-307 (1958).
Dibbern, E.M., Toublan, F.J., Suslick, K.S., "Formation and characterization of polyglutamate core-shell microspheres". Journal of the American Chemical Society 128, pp. 6540-6541 (2006).
Dong, W.F., Ferri, J.K., Adalsteinsson, T., Schonhoff, M., Sukhorukov, G.B., Mohwald, H., "Influence of Shell Structure on Stability, Integrity, and Mesh Size of Polyelectrolyte Capsules: Mechanism and Strategy for Improved Preparation" Chemistry of materials 17, pp. 2603-2611 (2005).
Farmer, P.J., Gidanian, S., Shahandeh, B., Di Bilio, A.J., Tohidian, N., Meyskens, J.R., "Melanin as a Target for Melanoma Chemotherapy: Pro-oxidant Effect of Oxygen and Metals on Melanoma Viability" Pigment cell research, 16, pp. 273-279 (2003).
Farnad, N., Farhadi, K., Voelcker, N., "Polydopamine Nanoparticles as a New and Highly Selective Biosorbent for the Removal of Copper (II) Ions from Aqueous Solutions" Water Air Soil Pollut. 223, pp. 3535-3544 (2012).
Gandolfi, O., Blum, J., "Antileukemic Platinum(II)-Catecholamine Complexes" Inorganica Chimica Acta 80, pp. 103-106 (1983).
Grinstaff, M.W., Suslick, K.S., "Air-filled proteinaceous microbubbles: Synthesis of an echo-contrast agent" Proceedings of the National Academy of Sciences of the United States of America 88, pp. 7708-7710 (1991).
Lee, H., Scherer, N.F., Messersmith, P.B., "Single-molecule mechanics of mussel adhesion" Proceedings of the National Academy of Sciences of the United States of America 103, pp. 12999-13003 (2006).
Lee, H., Dellatore, S.M., Miller, W.M., Messersmith, P.B.,"Mussel-Inspired Surface Chemistry for Multifunctional Coatings" Science 318, pp. 426-430 (2007).
Lee, H., Rho, J., Messersmith, P.B., "Facile Conjugation of Biomolecules onto Surfaces via Mussel Adhesive Protein Inspired Coatings" Advanced Materials 21, pp. 431-434 (2009).
Lee, S.S., Song, W., Cho, M., Puppala, H.L., Nguyen, P., Zhu, H., Segatori, L., Colvin, V.L., "Antioxidant Properties of Cerium Oxide Nanocrystals as a Function of Nanocrystal Diameter and Surface Coating" ACS Nano 7, pp. 9693-9703 (2013).
Lippitt, B., McCord, J.M., Fridovich, I., "The Sonochemical Reduction of Cytochrome C and Its Inhibition by Superoxide Dismutase" The Journel of Biological Chemistry 247, pp. 4688-4690 (1972).

(Continued)

*Primary Examiner* — Anna Falkowitz
(74) *Attorney, Agent, or Firm* — Symbus Law Group, LLC; Clifford D. Hyra

(57) ABSTRACT

The present invention provides a sonochemical irradiation-based method for the preparation of polydopamine (PDA) nanocapsules having reduced wall thickness and uniform size distribution, which may further comprise at least one payload; nanocapsules obtained by this method; and compositions thereof. Such compositions may be formulated for different purposes, e.g., as pharmaceutical compositions for various therapeutic or diagnostic purposes.

30 Claims, 24 Drawing Sheets

(56) References Cited

OTHER PUBLICATIONS

Liu, Q.Z., Yu, B., Ye, W.C., Zhou, F., "Highly Selective Uptake and Release of Charged Molecules by pH-Responsive Polydopamine Microcapsules" Macromolecular Bioscience 11, pp. 1227-1234 (2011).

Ochs, C.J., Hong, T., Such, G.K., Cui, J., Postma, A., Caruso, F., "Dopamine-Mediated Continuous Assembly of Biodegradable Capsules" Chemistry of Materials 23, pp. 3141-3143 (2011).

Postma, A., Yan, Y., Wang, Y., Zelikin, A.N., Tjipto, E., Caruso, F., "Self-Polymerization of Dopamine as a Versatile and Robust Technique to Prepare Polymer Capsules" Chemistry of Materials 21, pp. 3042-3044, (2009).

Ren, Y.H., Rivera, J.G., He, L.H., Kulkarni, H., Lee, D.K., Messersmith, P.B., "Facile, high efficiency immobilization of lipase enzyme on magnetic iron oxide nanoparticles via a biomimetic coating" BMC Biotechnology 11:63 (2011).

Shalev, T., Gopin, A., Bauer, M., Stark, R.W., Rahimipour, S., J., "Non-leaching antimicrobial surfaces through polydopamine bio-inspired coating of quaternary ammonium salts or an ultrashort antimicrobial lipopeptide" Journal of Materials Chemistry 22, pp. 2026-2032 (2012).

Skirtenko, N., Tzanov, T., Gedanken, A., Rahimipour, S., "One-Step Preparation of Multifunctional Chitosan Microspheres by a Simple Sonochemical Method" Chemistry of European Journal 16, pp. 562-567 (2010).

Skirtenko, N., Richman, M., Nitzan, Y., Gedanken, A., Rahimipour, S., "A facile one-pot sonochemical synthesis of surface-coated mannosyl protein microspheres for detection and killing of bacteriaw" Chemical Communications 47, pp. 12277-12279 (2011).

Suslick, K.S., Grinstaff, M.W., "Protein microencapsulation of nonaqueous liquids" Journal of American Chemical Society 112, pp. 7807-7809 (1990).

Szpoganicz, B., Gidanian, S., Kong, P., Farmer, P., "Metal binding by melanins: studies of colloidal dihydroxyindole-melanin, and its complexation by Cu(II) and Zn(II) ions" Journal of Inorganic Biochemistry 89, pp. 45-53 (2002).

Wong, M., Suslick, K.S., "Sonochemically Produced Hemoglobin Microbubbles" Materials Research Society Symposium Proceedings 372, pp. 89-94 (1995).

Xu, H., Liu, X., Wang, D., "Interfacial Basicity-Guided Formation of Polydopamine Hollow Capsules in Pristine O/W Emulsions—Toward Understanding of Emulsion Template Roles" Chemistry of Materials 23, pp. 5105-5110 (2011).

Yu, B., Wang, D.A., Ye, Q., Zhou, F., Liu, W., "Robust polydopamine nano/microcapsules and their loading and release behavior" Chemical Communications, pp. 6789-6791 (2009).

Zhang, L., Shi, J., Jiang, Z., Jiang, Y., Qiao, S., Li, J., Wang, R., Meng, R., Zhu, Y., Zheng, Y., "Bioinspired preparation of polydopamine microcapsule for multienzyme system construction" Green Chemistry 13, pp. 300-306 (2011).

Zhang, L., Wu, J., Wang, Y., Long, Y., Zhao, N., Xu, J., "Combination of Bioinspiration: A General Route to Superhydrophobic Particles" Journal of American Chemistry society 134, pp. 9879-9881 (2012).

\* cited by examiner

DOPAMINE NANOCAPSULES AND USES THEREOF

CROSS-REFERENCE TO RELATED APPLICATIONS

The present application claims the benefit of U.S. Provisional Patent Application No. 61/749,397, filed Jan. 7, 2013, the entire content of which being herewith incorporated by reference in its entirety as if fully disclosed herein.

TECHNICAL FIELD

The present invention relates to a method for the preparation of polydopamine (PDA) nanocapsules having reduced wall thickness and uniform size distribution using sonochemical irradiation, nanocapsules prepared by that method, and uses thereof.

BACKGROUND ART

PDA is a biomimetic polymer based on mussel adhesive protein, which is excreted by many marine organisms. It is produced by the self-polymerization of dopamine (DA) under oxidative and alkaline conditions, similar to those existing in seawater (Lee et al., 2007). The structure of PDA and the mechanism for its generation closely resemble those of melanin, which is generated from the polymerization of L-dopa.

The adhesive and cohesive properties of PDA are believed to be related to the reactivity of polyorthoquinoneindole, which forms covalent bonds with various substances via Schiff-base type reactions (with amine containing molecules) or Michael type reactions (with amine and thiol-containing molecules) (Scheme 1 in Appendix A). Moreover, the catecholic moiety of PDA can engage in hydrogen bonding, metal complexation, π-π interactions, and quinhydrone charge-transfer complexation (Waite, 1987). Recently, Messersmith et al. reported that PDA could be deposited as a thin adherent polymer film on different material surfaces, including metals, polymers and inorganic materials, converting them to versatile substrates for further ad-layer deposition of various compounds (Lee et al., 2007; Lee et al., 2006; Lee et al., 2009). The interfacial adhesion property of PDA coatings has been widely exploited to introduce new functionalities to materials for various applications (Ye et al., 2011; Chye Khoon et al., 2010; Kang et al., 2012; Chenglin et al., 2012; Sureshkumar et al., 2010; Ren et al., 2011). PDA has recently been utilized to coat different surfaces with antibacterial agents to generate antibacterial surfaces (Shalev et al., 2012).

The unique chemical properties of PDA have inspired researchers to explore its capability to form micro- and nano-capsules for different applications (Cui et al., 2010; Zhang et al., 2011; Ochs et al., 2011; Zhang et al., 2012; Postma et al., 2009; Yu et al., 2009; Cui et al., 2012). Postma et al. have used the template-assisted assembly methodology (Caruso et al., 1998) to polymerize DA on the surface of $SiO_2$ particles to generate hollow PDA nanocapsules after etching the template by acid treatment (Postma et al., 2009). Using a similar templating methodology, PDA micro- and nanocapsules have been constructed to selectively uptake and release charged molecules in response to external pH changes, so paving the way to new and highly specific drug delivery applications (Yu et al., 2009). Monodispersed PDA capsules with a diameter range of 0.4-2.4 μm were also prepared by emulsion templating using oil/water emulsion droplets containing 2% ammonia (Cui et al., 2010; Xu et al., 2011). This method avoids the use of harsh conditions to remove the template, which would otherwise be a limitation when biomolecules are present. The capsules were successfully loaded with functional substances, including magnetic nanoparticles ($Fe_3O_4$), quantum dots, and non-aqueous soluble drugs for potential biomedical applications. Using this methodology, PDA capsules whose surface was covalently immobilized with pH-cleavable polymer-drug conjugates were prepared for the intracellular delivery of doxorubicin as an anticancer agent (Cui et al., 2012).

Among various methods being developed for the preparation of micro- and nanocapsules, the sonochemical approach has gained considerable attention. Suslick and coworkers found a remarkably easy sonochemical technique for the preparation of both air-filled micro-bubbles and non-aqueous liquid-filled protein microspheres that were assembled from bovine serum albumin, hemoglobin, and human serum albumin (Suslick and Grinstaff, 1990; Grinstaff and Suslick, 1991; Wong and Suslick, 1995). Free radicals, such as superoxide radicals, generated during sonochemical irradiation (Del Duca et al., 1958; Lippitt et al., 1972), were suggested to be responsible for cross-linking the intermolecular Cys residues through disulfide bond formation, thereby generating the microsphere shell (Suslick and Grinstaff, 1990; Grinstaff and Suslick, 1991; Wong and Suslick, 1995). Similar procedures were also used to prepare microspheres from Cys-less proteins (Avivi and Gedanken, 2002; Dibbern et al., 2006) or even from the polysaccharide chitosan (Skirtenko et al., 2010). Non-covalent intermolecular interactions were suggested to assist microsphere formation.

SUMMARY OF INVENTION

In one aspect, the present invention relates to a method for the preparation of nanocapsules each comprising a shell obtained upon polymerization of a compound of the general formula I:

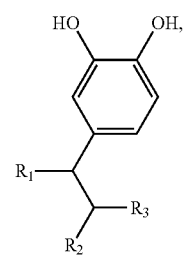

wherein
$R_1$ is H, OH, —$CH_2OH$, F or CN;
$R_2$ is H, $R_4$ or —$CH_2$—$R_4$;
$R_3$ is H, $NH_2$, OH, SH or COOH; and
$R_4$ IS $NH_2$, OH or SH,
provided that $R_2$ and $R_3$ are not both H,
preferably such a compound wherein both $R_1$ and $R_2$ are H, and $R_3$ is $NH_2$, i.e., 4-(2-aminoethyl)benzene-1,2-diol (dopamine),
said shell having a thickness of about 1 nm to about 20 nm, about 3 nm to about 15 nm, about 3 nm to about 10 nm, about 4 nm to about 6 nm, or about 5 nm,
said method comprising: (i) dissolving said compound in a basic aqueous solution; (ii) overlaying said aqueous solution with a non-aqueous solvent, thus forming a biphasic system; (iii) applying sonication to the aqueous-non-aqueous interface of said biphasic system thereby obtaining said nanocapsules; and (iv) isolating said nanocapsules.

The nanocapsules prepared by the method of the present invention may further comprise at least one, i.e., one, two, three or more, payload each independently encapsulated by said shell; and/or coordinated to functional groups on the outer surface of said shell, said functional groups being selected from OH, COOH, SH, $NH_2$, —NH— or =N—, and/or embedded within said shell; and/or linked to the outer surface of said shell, optionally via a linker. Such payloads may each independently be a metal atom or an ion or oxide thereof, a diagnostic agent, a targeting agent, a therapeutic agent, or a catalyst.

Thus, in certain embodiments, said at least one payload each independently is (i) encapsulated by said shell, and said method further comprises the step of dissolving or suspending said at least one payload in said non-aqueous solvent prior to sonication; (ii) coordinated to functional groups on the outer surface of said shell or embedded within said shell, and said method further comprises the step of dissolving said at least one payload in said aqueous solution prior to sonication; or (iii) linked to the outer surface of said nanocapsules, optionally via a linker, and said method further comprises the step of linking said at least one payload to said nanocapsules, optionally via said linker. In particular embodiments, the nanocapsules prepared by the method of the invention comprise more than one, e.g., two payloads, each as defined above. In a more particular such embodiment, one of said payloads are metal ions coordinated to functional groups on the outer surface of said shell, and another one of said payloads is coordinated to said metal ions, and said method further comprises the step of coordinating said another one of said payload to said metal ions after isolation of said nanocapsules.

In another aspect, the present invention provides nanocapsules obtained by the method defined above, e.g., nanocapsules each comprising a shell obtained upon polymerization of dopamine. The nanocapsules of the invention may further comprise one or more payloads as defined above, each independently encapsulated by said shell; and/or coordinated to functional groups on the outer surface of said shell; and/or embedded within said shell; and/or linked to the outer surface of said shell, optionally via a linker.

In a further aspect, the present invention provides a composition comprising nanocapsules as defined above, i.e., nanocapsules each comprising a shell obtained upon polymerization of a compound of the general formula I, e.g., dopamine, by the method defined above. Such compositions may be formulated for different purposes, depending on the particular payload or payloads comprised within, and the intended use, e.g., as pharmaceutical compositions for various therapeutic or diagnostic purposes.

In still a further aspect, the present invention provides an anti-bacterial or anti-fouling structure comprising a substrate having a surface and nanocapsules as defined above, each comprising a shell obtained upon polymerization of dopamine, adhered to said surface, wherein said nanocapsules each comprising at least one payload having antibacterial properties.

Peaks at wavenumber <630 cm$^{-1}$ can most probably be assigned as Cu—O and Cu—N bonds. Furthermore, the decrease in intensity of the peak at 2500-3500 by Cu(II) demonstrates that the NH group of PDA slightly shared in the coordination; (7C) Cyclic voltammograms of PDA-NS prepared in the presence or absence of CuSO$_4$. Measurements were carried out in phosphate buffered solution (100 mM, pH 7.4). The voltammogram of PDA shows a quasi-reversible electron transfer step at 0.225 V (vs. Ag/AgCl), which most likely represents a two-electron, two-proton process oxidation to form the corresponding reactive ortho-quinone derivative; (7D) Addition of CuSO$_4$ to the solution of PDA-NS caused to gradual decrease of the CV peak at 0.225 V, suggesting that the chelation of Cu ion by PDA is mediated through the catecholic hydroxyls.

Figure 8:
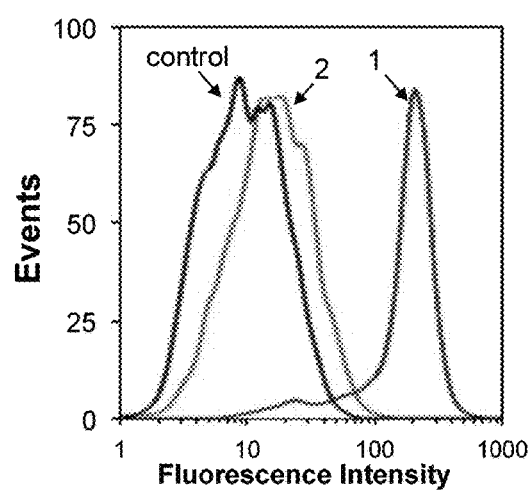

FIG. 8 shows chemical reactivity of PDA-NS toward nucleophilic addition. Flow-cytometry analyses of PDA-NS treated overnight with either Cys-expressing fluorescent probe 1 (red line) or Ala-expressing fluorescent probe 2 (green line). Naked PDA nanocapsules (black) were used as the control (see Experimental hereinafter).

Figure 9A:
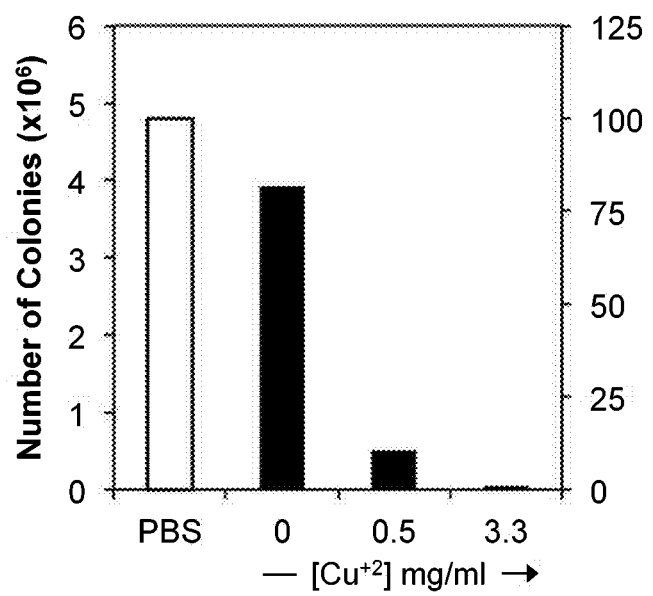
Figure 9B:
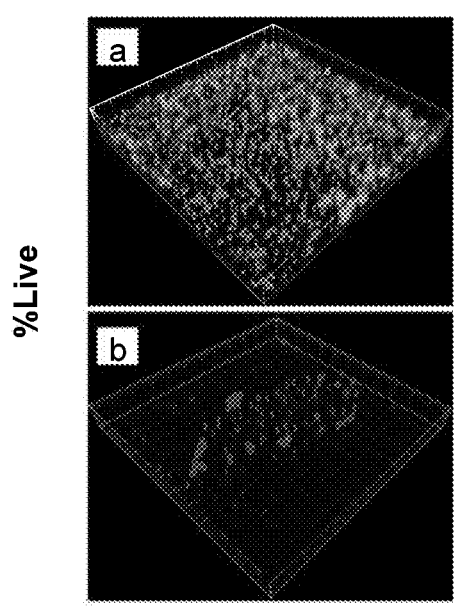

FIGS. 9A-9B show dose-dependent antibacterial activity of PDA-NS prepared with increasing amount of CuSO$_4$. *S. aureus* cells (1×10$^6$ cells ml$^{-1}$) were incubated for 2.5 h in PBS with capsules (50 µl, 12.5 mg/ml) containing different amounts of CuSO$_4$, and the number of bacteria was then determined by the spread plate technique (9A). 9B shows confocal laser scanning microscopy image of *S. aureus* treated for 15 min either with PBS (panel a) or Cu(II)-containing PDA-NS (panel b) and stained with a live/dead assay.

Figure 10A:
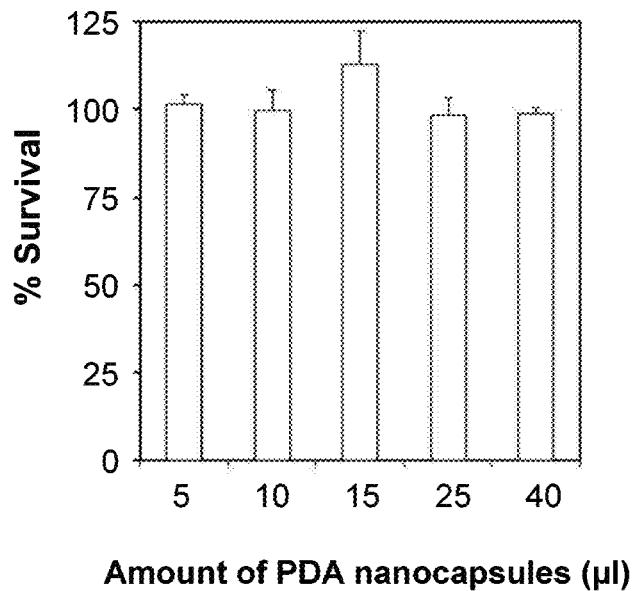
Figure 10B:
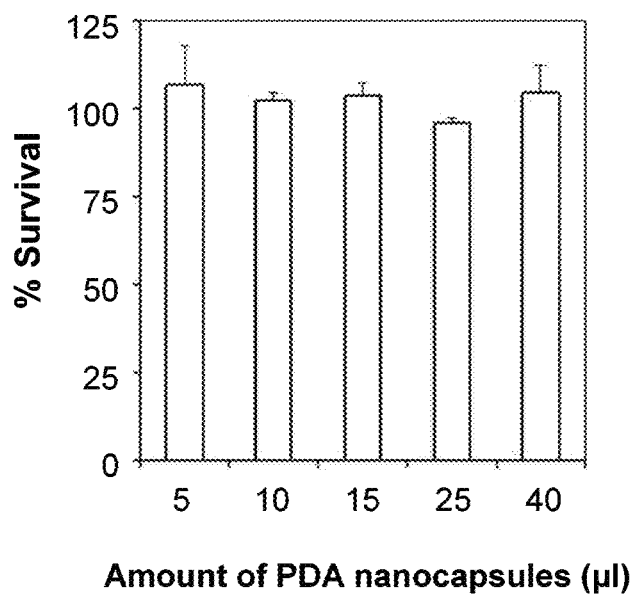

FIGS. 10A-10B show effect of PDA-NS prepared in the absence (10A) or presence (3.3 mg/ml; 10B) of CuSO$_4$ on the cell viability of PC12 cells. The percent survival results are shown as the mean±SD performed in quadruplicate.

Figure 11:
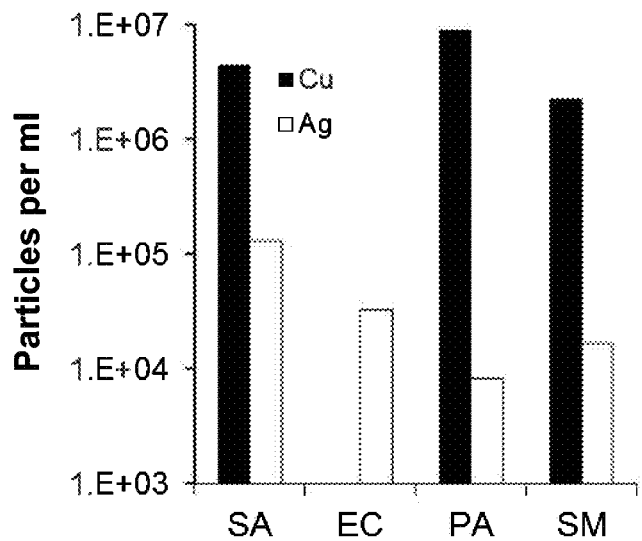

FIG. 11 shows that PDA-NS chelated with either Cu$^{2+}$ or Ag$^{1+}$ are potent antibacterial agents. Serial dilutions of PDA-NS were incubated at 37° C. with different bacteria (5×10$^5$ CFU/ml) in 96-well plate for 20 hours in a shaking incubator. The lowest number of particles that inhibited the growth of bacteria is shown in Y-axis.

Figure 12A:
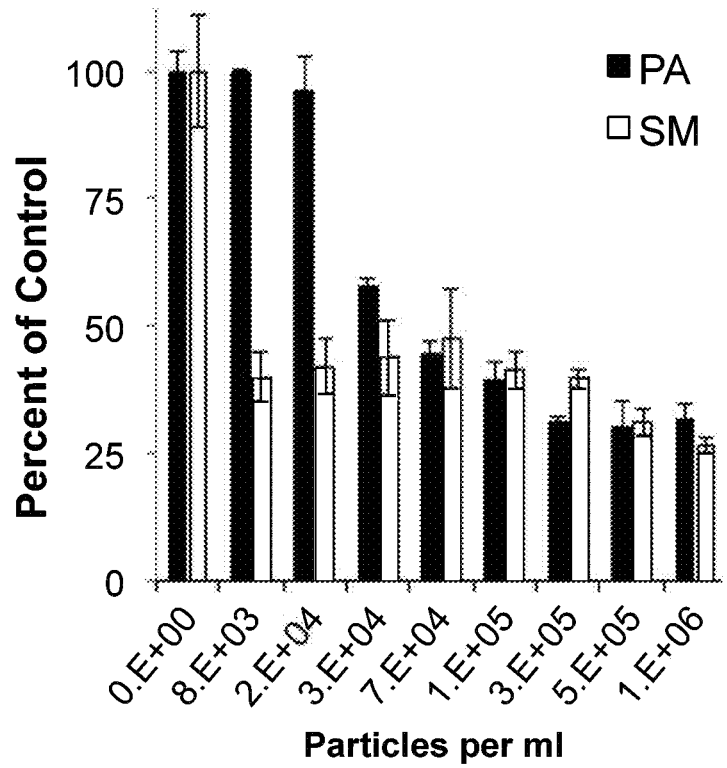
Figure 12B:
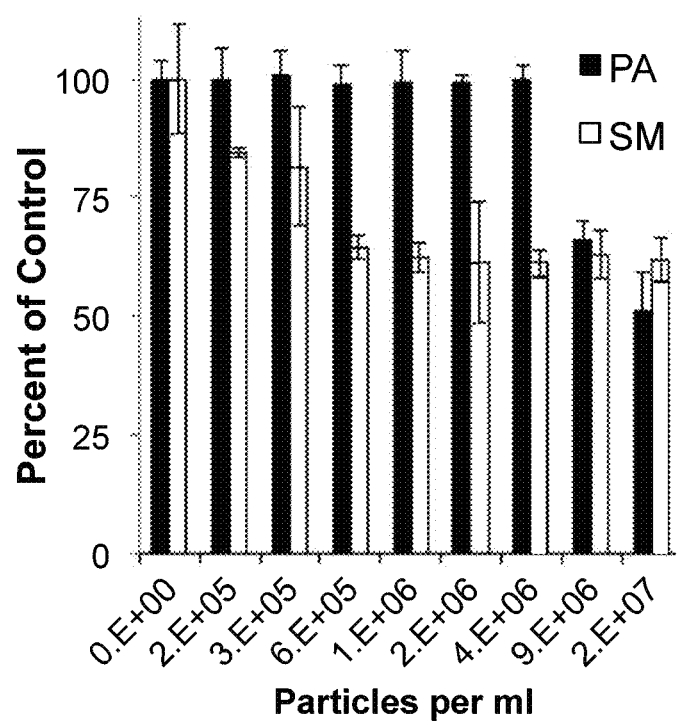
Figure 13A:
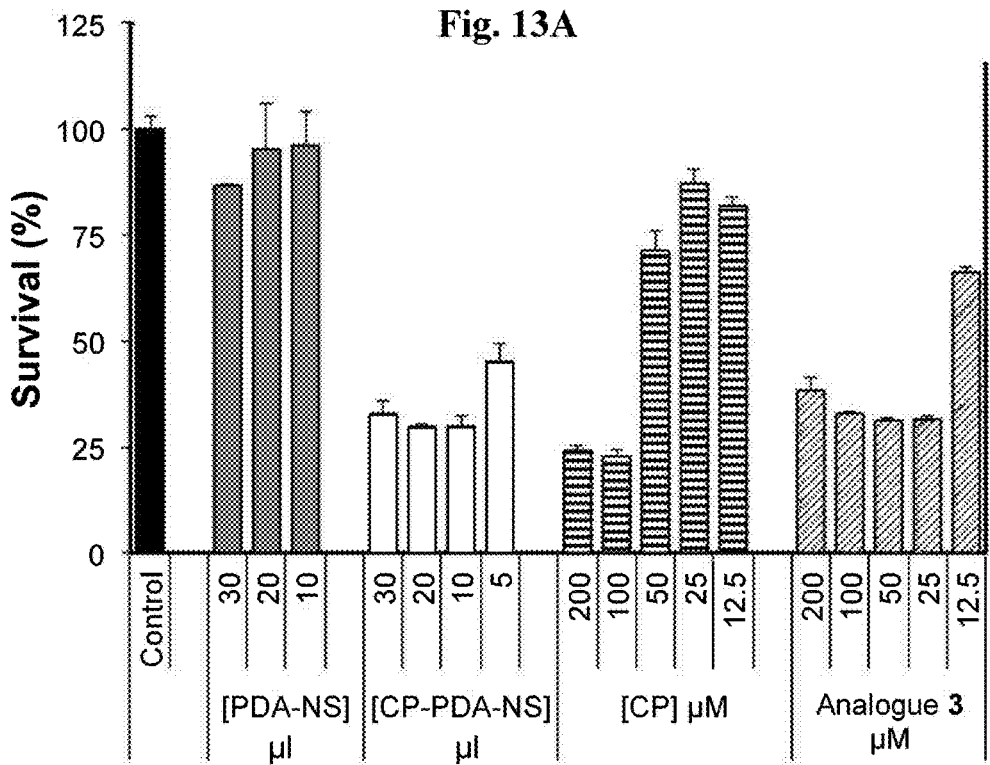
Figure 13B:
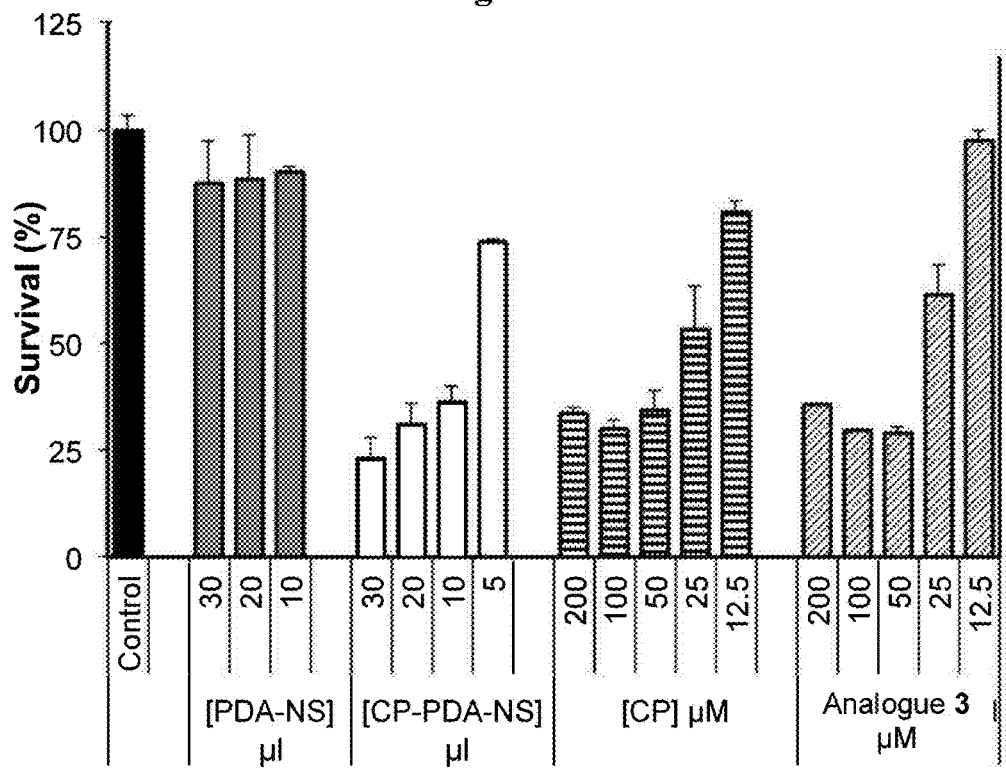
Figure 13C:
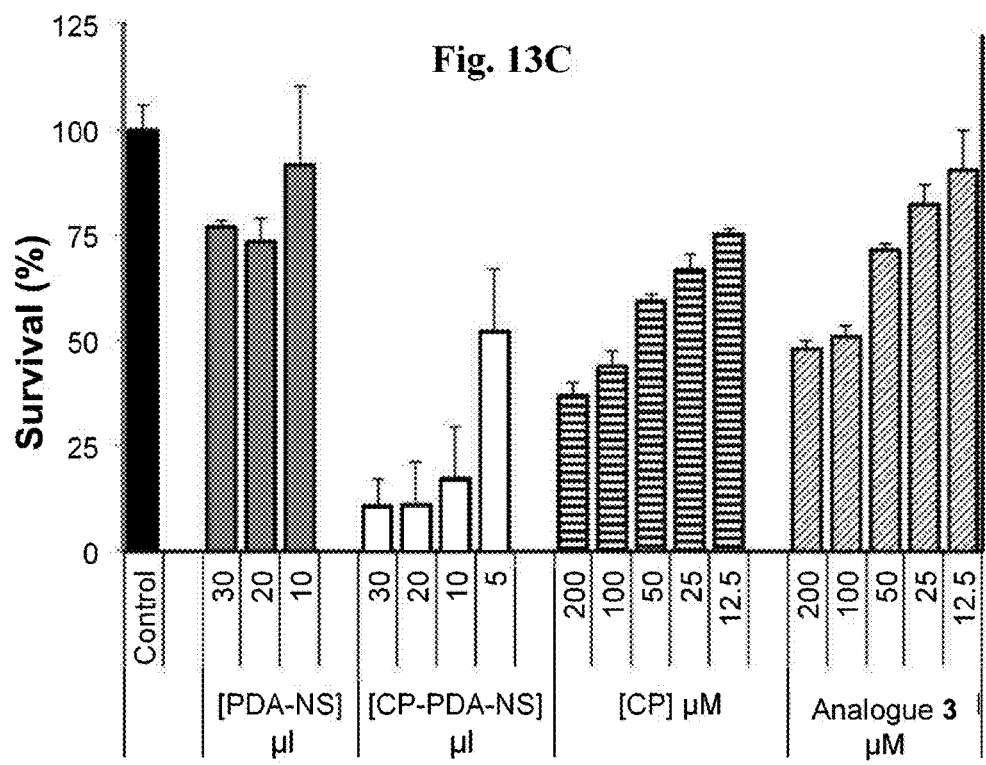
Figure 13D:
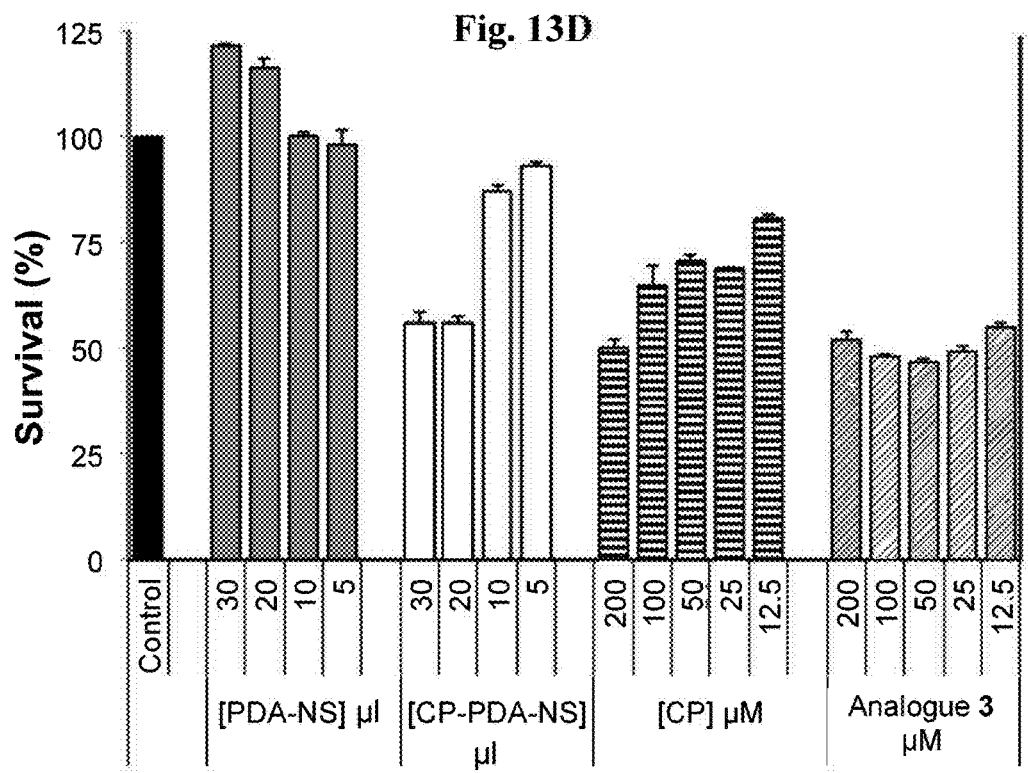

FIGS. 12A-12B show the antibiofilm activity of PDA-NS chelated with either Ag$^{1+}$ (12A) or Cu$^{2+}$ (12B). Serial dilutions of PDA-NS were incubated at 37° C. for overnight with 90 µl of bacteria (1×10$^7$ CFU/ml). Plates were then washed and stained with crystal violet and their absorbance was measured at 595 nm.

FIGS. 13A-13D show dose-dependent effect of cisplatin (CP), cisplatin-coated PDA-NS (CP-PDA-NS), analogue 3 (a cisplatin derivative) and PDA-NS on cell survival of rat adrenal pheochromocytoma cells (PC12, 13A); human breast cancer cells (MCF7, 13B); human prostate cancer cells (PC3, 13C); and mouse embryonic fibroblast cells (NIH-3T3, 13D). Cells were exposed to increasing amounts of CP, CP-PDA-NS, analogue 3 and PDA-NS for 24 h, and cell viability was then determined by the MTT assay. Results are expressed as a percentage of the control (untreated) cells and are reported as mean±SD.

Figure 14A:
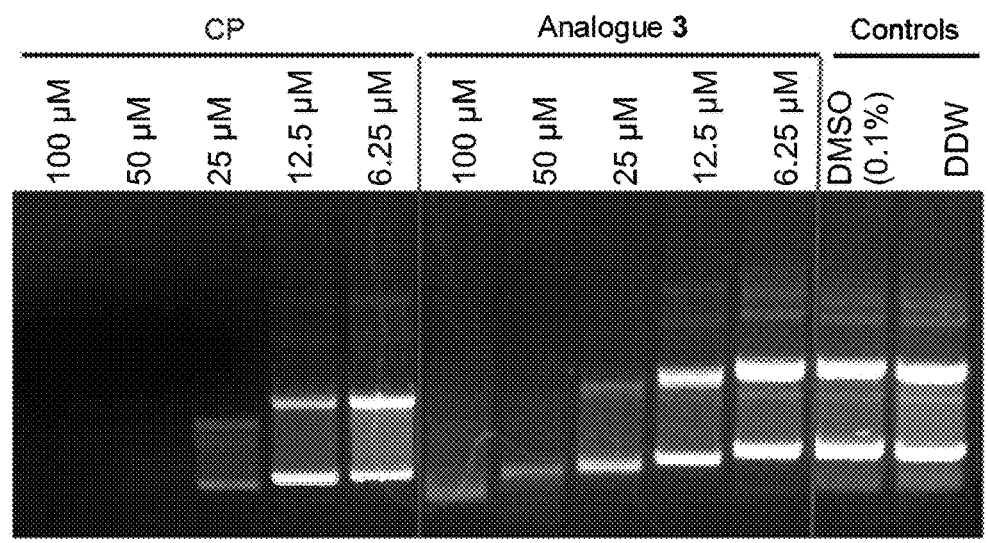
Figure 14B:
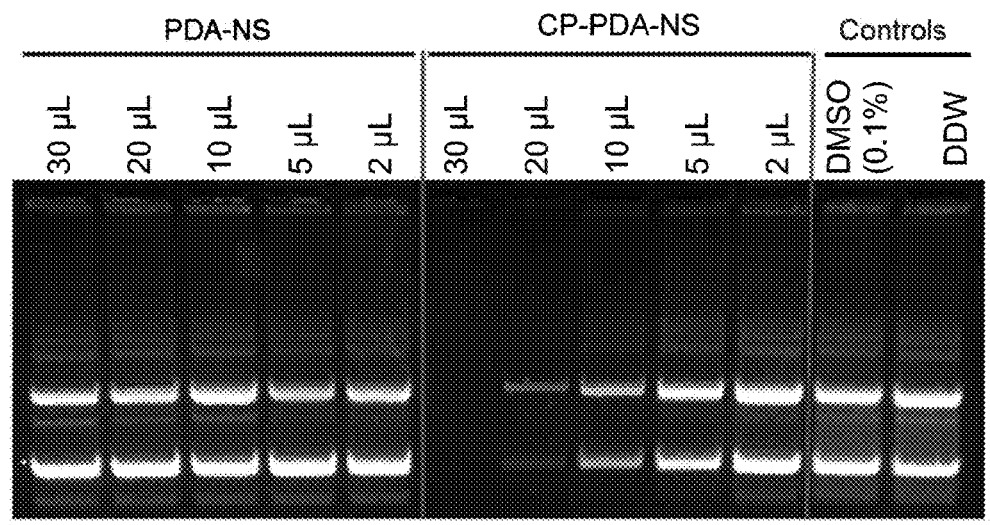
Figure 15A:
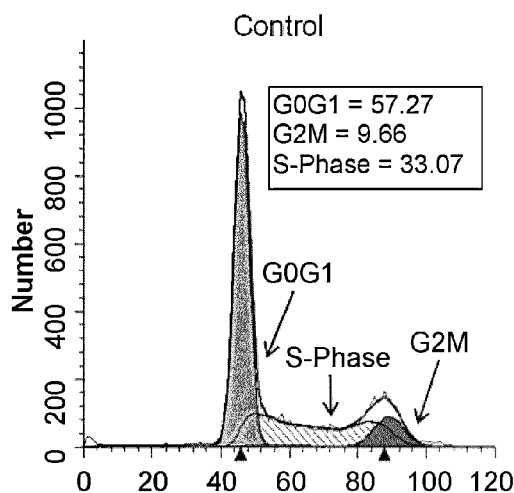
Figure 15B:
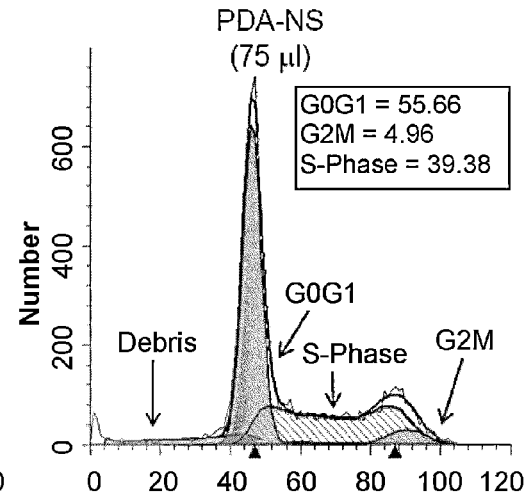
Figure 15C:
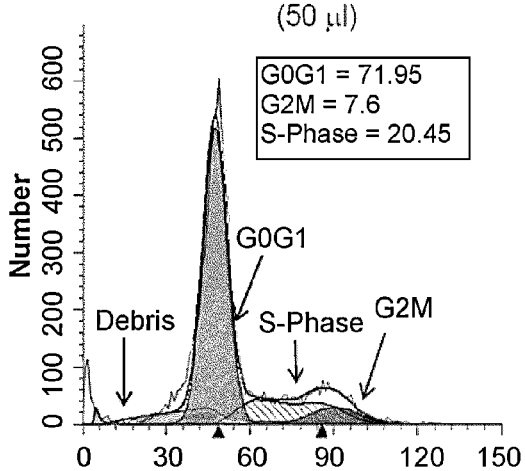
Figure 15D:
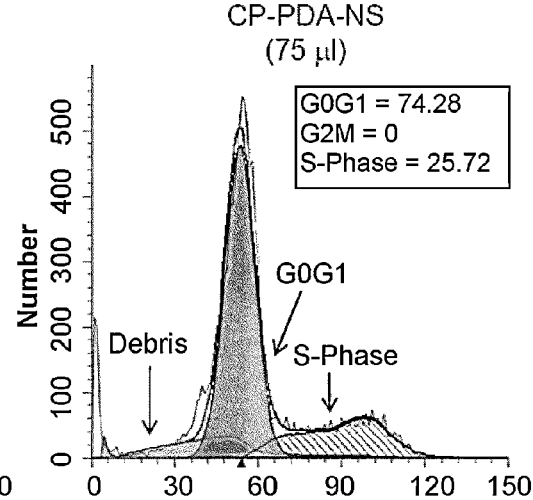

FIGS. 14A-14B show electrophoretic mobility of pcDNA™3.1-GFP plasmid in the presence of (14A) cisplatin (CP) or analogue 3 at different concentrations. (14B) Gel electrophoretic mobility of pcDNA™3.1-GFP plasmid in the presence of increasing amounts of PDA-NS or CP-PDA-NS. Control lanes 11 and 12 represent plasmid incubated either with 0.1% DMSO in DDW (lane 11) or in DDW (lane 12).

FIGS. 15A-15D shows cell cycle distribution analysis of MCF-7 cells after incubation with PDA-NS (15B) and cisplatin-containing PDA-NS (CP-PDA-NS, 50 (50 C) and 75 µl (15D)), vs. control (15A). Incubation of the cells with CP-PDA-NS (75 µl) significantly increases the fraction of G0G1 from 57% of normal cells to 74% and decrease the G2M population from 9.66 to 0. 15A shows control.

Figure 16A:
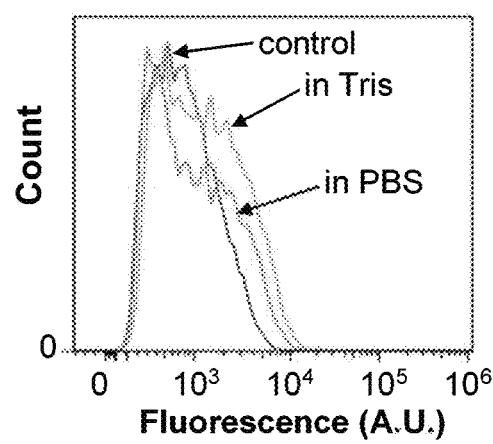
Figure 16B:
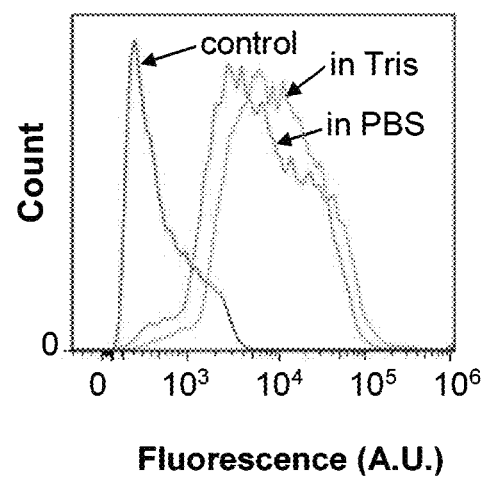

FIGS. 16A-16B show conjugation of the His-tagged NBD peptide described in Study 4 hereinafter to PDA-NS (16A) and Ni-chelated PDA-NS (16B) under different conditions. PDA-NS in PBS served as control. Incubation of PDA-NS with His6-NBD in either Tris buffer or PBS slightly increased the fluorescent signal most probably due to non-specific binding. Incubation of Ni-PDA-NS with His6-NBD in either Tris buffer or PBS significantly increased the fluorescent signal as compared to parent Ni-PDA-NS, implicating more efficient conjugation of His6-tagged molecules to Ni-PDA-NS as compared to unchelated NS.

Figure 17A:
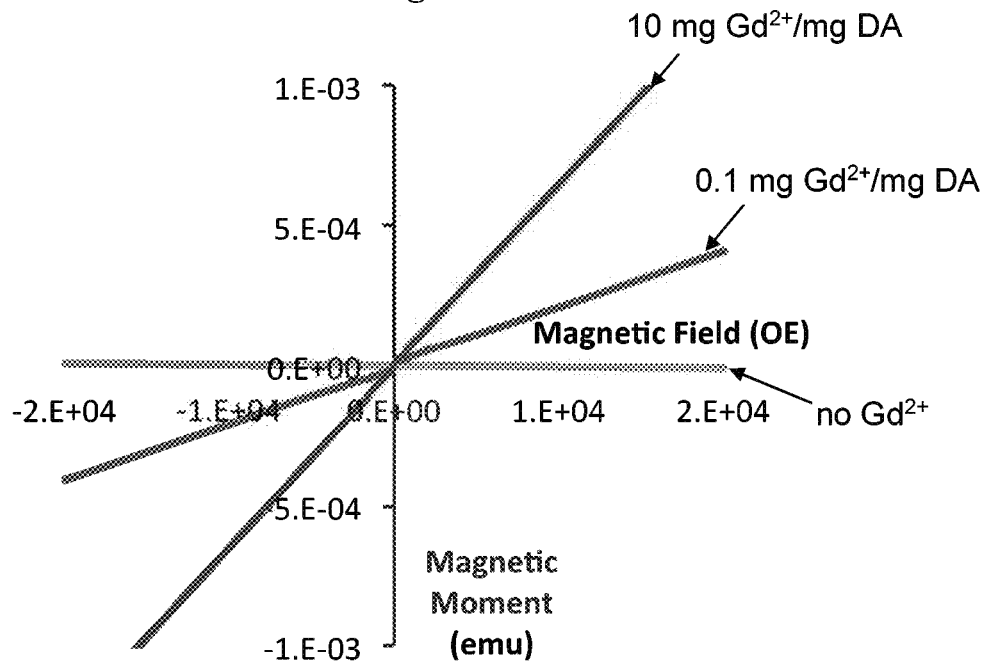
Figure 17B:
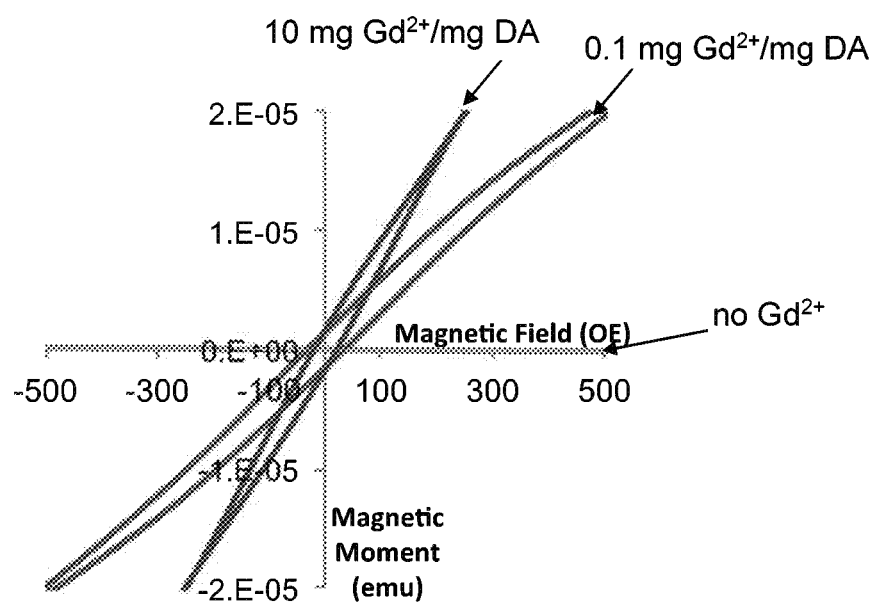
Figure 17C:
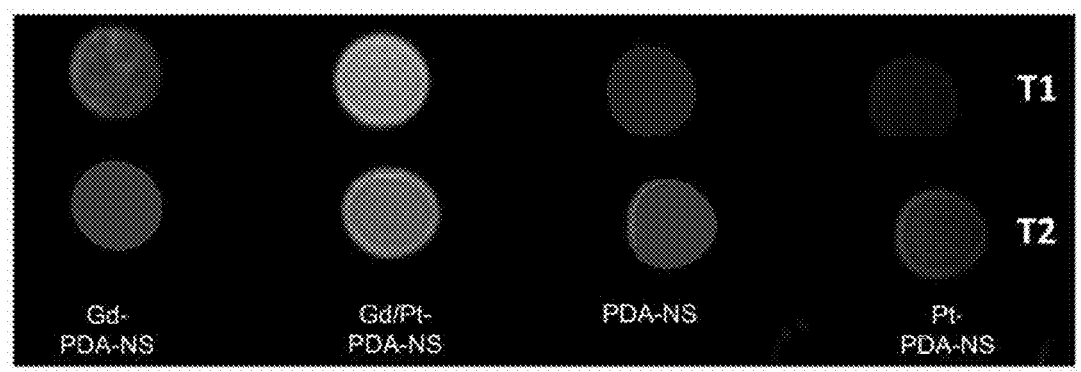

FIGS. 17A-17C show the magnetic properties (17A-17B) and MRI analysis (17C) of Gd-chelated PDA-NS. (17A) Changing of magnetic moment of particles under exposure to a varying magnetic field reveals that while non-metal PDA-NS are very slightly diamagnetic, PDA-NS prepared in the presence of 0.1 mg or 10 mg Gd$^{2+}$ per mg of DA significantly increase the magnetic susceptibility. Furthermore, a closer look at lower magnetic fields (17B) reveals hysteresis loops in both Gd-PDA-NS preparations, which is characteristic to ferromagnetic materials. (17C) MRI of different PDA-NS reveals that particles prepared with both Gd$^{2+}$ and Pt$^{2+}$ are strongly visible in both T1 and T2 modes of the MRI.

Figure 18A:
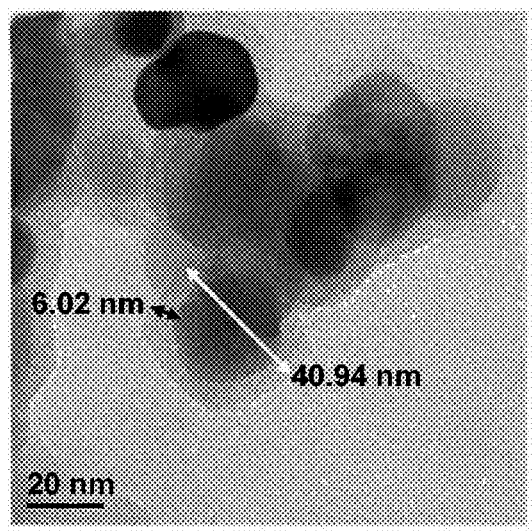
Figure 18B:
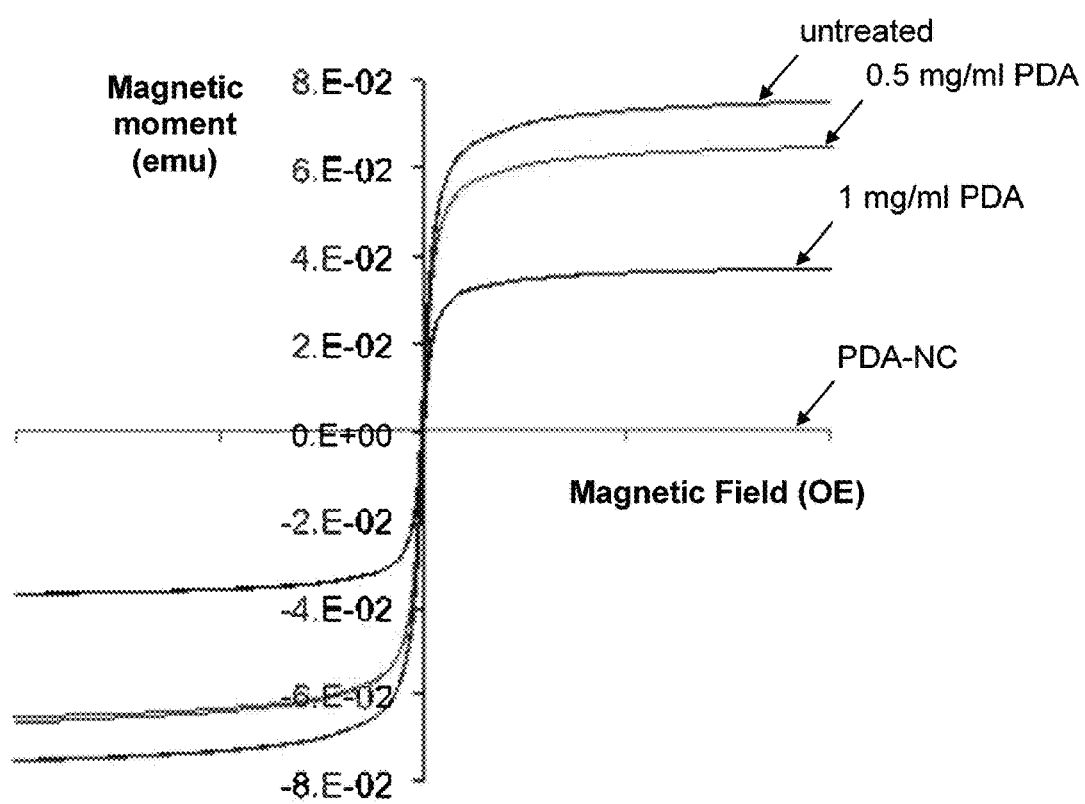

FIGS. 18A-18B show the magnetic properties of Fe$_3$O$_4$ encapsulated PDA-NS. (18A) TEM image of Fe$_3$O$_4$ particles coated with PDA (1 mg/ml), demonstrating a core consisting of a dark iron oxide with about 40 nm in diameter, and a shell composed of PDA with 6 nm thicknesses. (18B) Magnetic measurements of the Fe$_3$O$_4$ encapsulated PDA-NS. Untreated Fe$_3$O$_4$ particles show the strongest magnetic property, while Fe$_3$O$_4$ particles coated with 0.5 mg/ml or 1 mg/ml of PDA show slightly diminished magnetic property, although still retaining their ferromagnetic properties. PDA-NS show diamagnetic behavior and are shown as reference.

Figure 19:
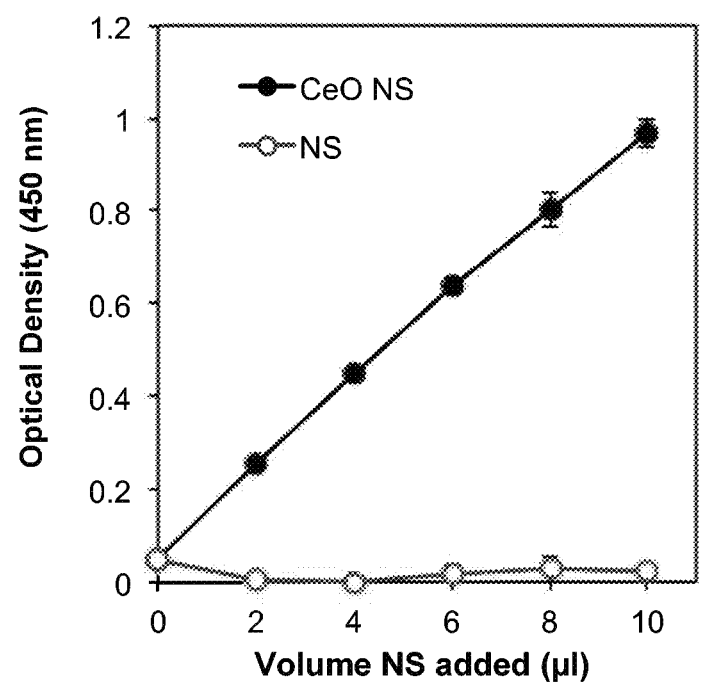

FIG. 19 shows oxidation of TMB by PDA-NS and CeO-doped PDA-NS.

DETAILED DESCRIPTION OF THE INVENTION

As found in accordance with the present invention, sonochemical irradiation of a dopamine solution in a two-phase system, utilizing a sonochemical technique based on that previously disclosed (Suslick and Grinstaff, 1990; Grinstaff and Suslick, 1991; Wong and Suslick, 1995), generates PDA capsules in only 6 min (or less) compared with the 24 h required using the classic emulsion methodology. Dynamic light scattering (DLS) studies suggest that the PDA capsules prepared by that method are significantly smaller than those prepared by other methods, and have uniform size distribution. Electron microscopy analyses reveal that the sonochemically-produced PDA capsules have significantly reduced shell thickness compared with that of PDA capsules prepared by emulsion or layer-by-layer methodologies, and yet thermogravimetric analyses demonstrate that they are as stable as PDA capsules produced by other methods, more particularly, have a 50% decomposition temperature (Td$_{50}$) of about 670° C. and 5% decomposition temperature (Td$_5$)

of about 209° C., as compared with 711° C. and 252.6° C., respectively (IPC-TM-650 Test Methods Manual, Thermal Stability).

In one aspect, the present invention thus relates to a method for the preparation of nanocapsules each comprising a shell obtained upon polymerization of a compound of the general formula I as defined above, said shell having a thickness of about 1 nm to about 20 nm, about 3 nm to about 15 nm, about 3 nm to about 10 nm, or about 5 nm, said method comprising: (i) dissolving said compound in a basic aqueous solution; (ii) overlaying said aqueous solution with a non-aqueous solvent, thus forming a biphasic system; (iii) applying sonication to the aqueous-non-aqueous interface of said biphasic system thereby obtaining said nanocapsules; and (iv) isolating said nanocapsules.

The nanocapsules isolated in step (iv) of the method defined above comprise a core consisting of said non-aqueous, i.e., organic, solvent, which is overcoated by a shell formed upon polymerization of a compound of the general formula I. The organic solvent composing the core can be replaced with water, if necessary, using any process or technology known in the art, e.g., by repeatedly precipitating the nanocapsules by suspending them in rising ratios of a polar solvent in water starting, for example, from a solution containing polar solvent:water in ratios starting from 25:75 to 100% of polar solvent, and then resuspending in deionized water (DDW), as described in Experimental hereinafter. Examples of polar solvents that may be used include, without being limited to, acetone, acetonitrile, ethyl acetate, methanol, ethanol, n-propanol and isopropanol.

The terms "capsules", "particles", and "nanocapsules" or "nanospheres" (NS), as used herein interchangeably, refer to a sphere-like structures obtained by the method of the present invention and having a diameter of, e.g., about 200 nm to about 1800 nm, about 300 nm to about 1000 nm, about 400 nm to about 800 nm, about 450 nm to about 650 nm, or about 500 to about 550 nm. The sphere-like nanocapsules have a core and a shell overcoating said core, wherein said shell is obtained upon polymerization of a compound of the general formula I as defined above, e.g., dopamine (see Scheme 1), and has a thickness of about 1 nm to about 20 nm, about 3 nm to about 15 nm, about 3 nm to about 10 nm, about 4 nm to about 6 nm, or about 5 nm. Capsules comprising shells obtained upon polymerization of dopamine are also referred to herein as "sonochemically-produced PDA nanocapsules", "PDA capsules" or "PDA nanocapsules" (PDA-NS).

The term "about", as used herein with respect to the diameter of the nanocapsules obtained by the method of the invention or their shell thickness, means within an acceptable error range for a particular value as determined by one of ordinary skill in the art, which will depend in part on how the value is measured or determined, i.e., the limitations of the measurement system. For example, "about" can mean a range of up to 20%, 15%, 10%, or up to 5%, i.e., 5%, 4%, 3%, 2% or 1% of a given value.

In certain embodiments, the nanocapsules prepared by the method of the present invention comprise a shell obtained upon polymerization of a compound of the general formula I as defined above, wherein $R_1$ is H. In certain particular such embodiments, $R_2$ is H; and $R_3$ is $NH_2$, OH, SH or COOH, preferably $NH_2$. In other particular such embodiments, $R_3$ is H; $R_2$ is $CH_2$—$R_4$; and $R_4$ is $NH_2$, SH or OH. Preferred nanocapsules prepared by this method are those comprising a shell obtained upon polymerization of a compound of the general formula I, wherein both $R_1$ and $R_2$ are H, and $R_3$ is $NH_2$, i.e., dopamine. Such preferred nanocapsules may have a 50% decomposition temperature ($Td_{50}$) of about 670° C. and 5% decomposition temperature ($Td_5$) of about 209° C.

The term "decomposition temperature", as used herein with respect to the nanocapsules prepared by the method of the present invention, refers to the temperature at which the nanocapsules chemically decompose. The term "50% decomposition temperature" ($Td_{50}$) is defined as the temperature at which 50% of the shell of said nanocapsules decomposes under inert atmosphere with a heating rate of 1° C./min; and the term "5% decomposition temperature" ($Td_5$) is defined as the temperature at which 5% of the shell of said nanocapsules have started decomposing under the above condition.

As shown herein, sonochemically-produced PDA capsules can effectively chelate various metal ions, including copper ions with the amount of chelated copper correlating directly with the fast bactericidal activity of the nanocapsules; and can also be loaded with non-aqueous soluble compounds and thus useful for drug delivery and imaging applications. As further demonstrated, the shell of the capsules preserves the reactivity of PDA toward nucleophiles under mild conditions, which should enable facile modification of their surface for different applications such as targeted drug delivery.

The nanocapsules prepared by the method of the present invention, as defined above, may thus further comprise at least one, i.e., one, two, three or more, payload each independently encapsulated by said shell; and/or coordinated to functional groups on the outer surface of said shell, said functional groups being selected from OH, COOH, SH, $NH_2$, —NH— or =N—; and/or embedded within said shell; and/or linked to the outer surface of said shell, optionally via a linker. In certain embodiments, said at least one payload each independently is (i) encapsulated by said shell, and said method further comprises the step of dissolving or suspending said at least one payload in said non-aqueous solvent prior to sonication; (ii) coordinated to functional groups on the outer surface of said shell or embedded within said shell, and said method further comprises the step of dissolving said at least one payload in said aqueous solution prior to sonication; or (iii) linked, either covalently or non-covalently, to the outer surface of said nanocapsules, optionally via a linker, and said method further comprises the step of linking said at least one payload to said nanocapsules, optionally via said linker.

Non-limiting examples of payloads that may be comprised within the nanocapsules prepared by the method of the invention include metal atoms or ions or oxides thereof, diagnostic agents, i.e., molecules that their presence can be detected directly or via an imaging method, targeting agents, i.e., molecules capable of directing the nanocapsules to which they are linked to a predefined target, therapeutic agents, and catalysts.

Examples of metal atoms include, without being limited to, transition metals such as Os, Ru, Fe, Pt, Pd, Ni, Ir, Rh, Co, Cu, Re, Tc, Mn, V, Nb, Ta, Hf, Zr, Cr, Mo, W, Ti, Sc, Ag, Au and Y; lanthanides such as La, Ce, Pr, Nd, Pm, Sm, Eu, Gd, Tb, Dy, Ho, Er, Tm, Yb and Lu; actinides such as Ac, Th, Pa, U, Np, Pu, Am, Cm, Bk, Cf, Es, Fm, Md, No and Lr; and main group element metal such as Zn, Ga, Ge, Al, Cd, In, Sn, Sb, Hg, Tl or Pb.

Non-limiting examples of diagnostic agents include dyes such as 9-diethylamino-5-benzo[α]phenoxazinone (Nile-red dye); fluorophores such as 3-mercapto-2-(14-(7-nitrobenzo [c][1,2,5]oxadiazol-4-ylamino)-5-oxo-3,9,12-trioxa-6-aza-tetradecanamido) propanamide; luminophores; heavy atoms; quantum dots; radioactive isotopes; and contrast agents. Examples of targeting agents include, without limiting, proteins, peptides and peptidomimetics such as arginine-glycine-aspartic acid (RGD)-containing peptides and peptidomimetics, amino-acid sequences, antibodies or fragments thereof such as Fab fragments and antigen binding sites of antibodies, single-chain variable fragments of antibodies, nucleotide sequences, DNA sequences, RNA sequences, peptide nucleic acid (PNA) sequences, carbohydrates, and steroids. Examples of therapeutic agents include, without being limited to, antibacterial agents and antibacterial enzymes such as lysostaphin and lysozyme; antiviral agents; antifungal agents; anticancer agents such as cisplatin or a derivative thereof, e.g., the derivative herein identified analogue 3 (see Appendix A), anthracycline chemotherapeutic agents such as doxorubicin (adriamycin), daunorubicin, epirubicin, idarubicin and mitoxantrone, mitotic inhibitors such as paclitaxel, topoisomerase I inhibitors such as camptothecin, and topoisomerase II inhibitors such as ellipticine; photosensitizers; vitamins; and hormones.

The term "peptidomimetic" as used herein refers to a small peptide-like chain designed to mimic a peptide, which typically arises from modification of an existing peptide or by designing a similar system that mimics peptides.

In certain embodiments, the nanocapsules prepared by the method of the invention comprise more than one, e.g., two, payloads, each as defined above. In particular such embodiments, the nanocapsules each comprises two payloads, wherein one of said payloads are metal ions coordinated to functional groups on the outer surface of said shell, and another one of said payloads is coordinated to said metal ions, and said method further comprises the step of coordinating said another one of said payloads to said metal ions after isolation of said nanocapsules.

In another aspect, the present invention provides nanocapsules obtained by the method defined above, i.e., nanocapsules each comprising a shell obtained upon polymerization of a compound of the general formula I and optionally further comprising at least one payload as defined above, each independently encapsulated by said shell; and/or coordinated to functional groups on the outer surface of said shell; and/or embedded within said shell; and/or linked, either covalently or non-covalently, to the outer surface of said shell, optionally via a linker.

In certain embodiments, the nanocapsules of the present invention are sonochemically-produced PDA nanocapsules prepared by the method of the invention upon polymerization of dopamine. In particular such embodiments, the nanocapsules of the invention each further comprises at least one, i.e., one, two, three or more, payload as defined above each independently encapsulated by said shell; and/or coordinated to OH groups on the outer surface of said shell or to the nitrogen atom of the indole moiety; and/or embedded within said shell; and/or linked to the outer surface of said shell, optionally via a linker. The term "OH groups" representing functional groups on the outer surface of the shell of sonochemically-produced PDA capsules refers to both the phenolic OH groups and/or their oxidized form, i.e., the quinone carbonyl groups. It should thus be understood that a payload can be coordinated to the two phenolic OH (or O⁻) groups, to a phenolic OH group and an oxygen atom of the quinone carbonyl (formed upon oxidation of the second OH group), or to the two quinone carbonyls, as shown in Scheme 1.

In certain particular embodiments, the nanocapsules of the present invention are PDA-NS each further comprising, as a payload, metal ions coordinated to OH groups on the outer surface of said shell, or atoms or an oxide of said metal embedded within said shell. As shown herein, such PDA-NS show crystallinity, e.g., in X-ray diffraction (XRD) and in high-resolution transmission electron microscopy (HRTEM) analyses.

The term "crystallinity", as used herein, refers to the degree of structural order in the nanocapsules of the present invention, as shown and can be measured, e.g., in XRD and/or HRTEM analysis, and it is indicative for a population or plurality of nanocapsules as defined above rather than for a particular specific nanocapsule. According to the present invention, a nanocapsule population is considered crystalline if at least 10%, 20%, 30%, 40%, 50%, 60%, 70%, 80%, 90%, or 95%, but preferably at least 50%, 60%, 70%, 80%, 90% or 95%, of the population show crystallinity.

Examples 1-2 hereinafter show PDA-NS comprising, as a payload, $Cu^{2+}$ or $Ag^{+1}$ ions coordinated to OH groups on the outer surface of the shell or to the N atom of the indole moiety, and further demonstrates their antibacterial activity; example 4 shows PDA-NS comprising, as a payload, $Ni^{2+}$ ions coordinated to OH groups of the outer surface of the shell or to the N atom of the indole moiety, and further demonstrates the coordination of a His-tagged peptide to said $Ni^{2+}$ ions; example 5 shows PDA-NS comprising, as a payload, $Gd^{2+}$ ions coordinated to OH groups of the outer surface of the shell or to the N atom of the indole moiety, and further demonstrates their possible use in imaging applications; and example 7 shows PDA-NS doped with a cerium oxide ($CeO/CeO_2$), i.e., PDA-NS comprising, as a payload, a cerium oxide embedded within said shell, for use, e.g., as catalysts in certain reactions.

In certain specific embodiments, the nanocapsules of the invention are PDA-NS each further comprising, as a payload, $Cu^{2+}$, $Fe^{2+}$, $Fe^{3+}$, $Zn^{2+}$, $Mg^{2+}$, $Mn^{2+}$, $Ag^{+1}$, $Ni^{2+}$, $Gd^{2+}$, $Ce^{2+}$ or $Ce^{4+}$ ions coordinated to OH groups on the outer surface of said shell or to the N atom of the indole moiety, or Cu, Fe, Zn, Mg, Mn, Ag, Ni, Gd or Ce atoms or an oxide thereof embedded within said shell.

In other particular embodiments, the nanocapsules of the present invention are PDA-NS each further comprising at least one payload each independently is covalently linked to the outer surface of said shell, optionally via a linker. According to the present invention, a payload linked to the outer surface of the shell can be linked by nucleophilic addition either directly to the aromatic ring as demonstrated in Scheme 1 (Lee et al., 2006; Lee et al., 2007; Shalev et al., 2012), or to any one of the functional groups available upon polymerization of the compound of the general formula I, more particularly, to an OH group or its oxidized form (Scheme 1), i.e., a carbonyl group, or to the N atom of the indole moiety, in the case of PDA-NS, as well as to COOH, SH or $NH_2$ group in case the compound of the general formula I is a dopamine derivative wherein at least one of $R_1$ and $R_2$ is not H and/or $R_3$ is not $NH_2$.

The linker through which the payload may be covalently linked to the outer surface of said shell is a divalent moiety, e.g., a divalent moiety of a nucleotide, a nucleotide sequence, an amino acid, a DNA, a peptide nucleic acid (PNA), an RNA, a peptide consisting of two, three, four, five, or more amino acid residues, a carbohydrate, a straight or branched polyethylene glycol (PEG), or a compound comprising at least one of the aforesaid.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl) alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl) alanine, 3-(6-bromoindolyl)alanine, 3-(5-bromoindolyl) alanine, azidohomoalanine, p-chlorophenylalanine, α-aminocaprylic acid, O-methyl-L-tyrosine, N-acetylgalactosamine-α-threonine, and N-acetylgalactosamine-α-serine.

The term "peptide" as used herein refers to a short chain of amino acid monomers linked by peptide bonds, i.e., the covalent bond formed when a carboxyl group of one amino acid reacts with an amino group of another. Such peptides, when consisting of more than 50 amino acid monomers, can also be classified as proteins, more particularly, proteins of low or medium molecular weight.

The term "peptide nucleic acid" as used herein refers to a synthetic homolog of a nucleic acid in which the phosphate-sugar polynucleotide backbone is replaced by a flexible pseudo-peptide polymer to which the nucleobases are linked.

The term "carbohydrate" as used herein refers to a molecule containing carbon, hydrogen and oxygen atoms, which can be cyclic or linear, saturated or unsaturated, and substituted or unsubstituted. Preferably, the carbohydrate comprises one or more saccharide residues. The term "saccharide residue" as used herein encompasses any residue of a sugar moiety, including monosaccharides, oligosaccharides and polysaccharides. Alternatively, the saccharide can be a saccharide derivative such as, but not limited to, glucosides, ethers, esters, acids and amino saccharides.

Monosaccharides consist of a single sugar molecule which cannot be further decomposed by hydrolysis. Examples of monosaccharides include, without limitation, pentoses such as arabinose, xylose and ribose. Oligosaccharides are chains composed of saccharide units, e.g., up to nine saccharide units. Examples of oligosaccharides include, without limitation, disaccharides such as sucrose, maltose, lactose and cellobiose; trisaccharides such as mannotriose, raffinose and melezitose; and tetrasaccharides such as amylopectin, Syalyl Lewis X (SiaLex) and the like. Polysaccharides are compounds consisting of 10 or more saccharide units held together by glycoside bonds, e.g., starch, glycogen, cellulose, gum arabic, agar and chitin.

In further particular embodiments, the nanocapsules of the present invention are PDA-NS each further comprising at least one payload each independently is non-covalently linked to the outer surface of said shell. Non-limiting examples of non-covalent linkages include hydrophobic interactions, polar interactions, magnetic interactions, hydrogen-bond interactions, electrostatic interactions, and Van-der-Waals interactions.

Example 3 shows PDA-NS comprising, as a payload, the cisplatin analogue herein identified analogue 3 covalently linked to the aromatic ring or the polymerized dopamine molecules, and further demonstrates their cytotoxic activity against certain cancer cell lines.

Example 6 shows PDA-NS comprising, as a payload, $Fe_3O_4$ nanopowder encapsulated by said shell, and further demonstrates that these nanocapsules are ferromagnetic and can thus be used for imaging.

In other specific embodiments, the nanocapsules of the invention are PDA-NS each further comprising, as a payload, (i) a dye such as Nile-red encapsulated by said shell; or (ii) a magnetite such as $Fe_3O_4$ or $Fe_2O_3$ encapsulated by said shell; or (iii) a fluorescent probe such as 3-mercapto-2-(14-(7-nitrobenzo[c] [1,2,5]oxadiazol-4-ylamino)-5-oxo-3,9,12-trioxa-6-azatetradecanamido) propanamide covalently linked to the outer surface of the shell; or (iv) cisplatin or a derivative thereof covalently linked to the outer surface of said shell.

In further specific embodiments, the nanocapsules of the invention are PDA-NS each further comprising, as one payload, Ni ions coordinated to OH groups on the outer surface of said shell or to the N atom of the indole moiety (herein identified Ni-coated PDA-NS), and as another payload, a His-tagged protein or peptide, e.g., an antibody or a fragment thereof, coordinated to said Ni ions. In one particular example of such an embodiment, an antibody such as trastuzumab (Herceptin®), which selectively binds HER2 overexpressing cancers and recombinantly produced, is engineered to express a His-tag (e.g., His6-tag) at either C- or N-terminals (also available through AbD Serotec, Bio-Rad), and is then incubated under physiological conditions with Ni-coated PDA-NS, following which the His-tagged antibody is coordinated to said Ni ions (the excess of the antibody is washed away, e.g., by centrifugation). The anticancer activity of the conjugated Ni-coated PDA-NS can be evaluated on cells overexpressing HER2 ligand. In another particular example of such an embodiment, a recombinantly produced antibacterial enzyme such as lysostaphin (Becker et al., 2008) or lysozyme containing a His-tag fragment is incubated with Ni-coated PDA-NS, following which the His-tagged lysostaphin or lysosyme is coordinated to said Ni ions (the excess of the enzyme is washed away). The antibacterial activity (MIC) of the conjugated Ni-coated PDA-NS can be determined using any suitable assay available, e.g., the classical microtitre plate-based antibacterial assay. Such conjugated PDA-NS are expected to exhibit antibacterial activity that is similar to that of free lysostaphin or lysosyme, respectively, with higher stability. Moreover, the adhesive properties of the PDA-NS could be exploited to apply the conjugated PDA-NS to different surfaces thus rendering those surfaces antibacterial.

In a further aspect, the present invention provides a composition comprising nanocapsules as defined above, i.e., nanocapsules each comprising a shell obtained upon polymerization of a compound of the general formula I by the method of the present invention. In certain embodiments, the composition of the invention comprises sonochemically-produced PDA nanocapsules.

The compositions of the invention may be formulated for different purposes, depending on the particular payload or payloads comprised within, and the intended use. Particular such compositions further comprise a pharmaceutically acceptable carrier, and are formulated for various therapeutic or diagnostic purposes. More particular such pharmaceutical compositions are those comprising PDA-NS.

The pharmaceutical compositions of the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the nanocapsules as defined above either in their basic form or when further comprising one or more payloads as defined above, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients.

The pharmaceutical compositions of the invention can be formulated for any suitable route of administration, but they are preferably formulated for parenteral, e.g., intravenous, intraarterial, intramuscular, intraperitoneal, intrathecal, intrapleural, intratracheal, subcutaneous, transdermal, or inhalational administration. The dosage will depend on the state of the patient, and will be determined as deemed appropriate by the practitioner.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

The pharmaceutical compositions of the invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166, 452 and 4,265,874 to form osmotic therapeutic tablets for control release. The pharmaceutical composition of the invention may also be in the form of oil-in-water emulsion.

Pharmaceutical compositions according to the invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

The pharmaceutical compositions of the invention may be formulated for controlled release of the active agent or the payload itself. Such compositions may be formulated as controlled-release matrix, e.g., as controlled-release matrix tablets in which the release of a soluble agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is a depot system based on a biodegradable polymer, wherein as the polymer degrades, and the active agent or the payload itself is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

In certain embodiments, the present invention provides a pharmaceutical composition comprising nanocapsules each comprising a shell obtained upon polymerization of a compound of the general formula I, wherein said nanocapsules further comprise, as a payload, metal ions having antibacterial properties such as $Cu^{2+}$, $Fe^{2+}$, $Mg^{2+}$ or $Ag^{+1}$ coordinated to functional groups on the outer surface of said shell, or Cu, Fe, Mg or Ag atoms, respectively, embedded within said shell. Particular such compositions are those comprising PDA-NS, wherein said metal ions are coordinated to OH groups on the outer surface of said shell or to the N atom of the indole moiety, or said atoms are embedded within said shell. Such pharmaceutical compositions are useful for treatment of bacterial infection. The present invention thus further relates to a method for treatment of a bacterial infection in an individual in need, comprising administering to said individual a therapeutically effective amount of nanocapsules as defined above, wherein said nanocapsules further comprise, as a payload, metal ions having antibacterial properties such as $Cu^{2+}$, $Fe^{2+}$, $Mg^{2+}$ or $Ag^{+1}$ coordinated to functional groups on the outer surface of said shell, or Cu, Fe, Mg or Ag atoms, respectively, embedded within said shell.

In certain embodiments, the present invention provides a pharmaceutical composition comprising nanocapsules each comprising a shell obtained upon polymerization of a compound of the general formula I, wherein said nanocapsules further comprise, as a payload, $Gd^{2+}$ ions coordinated to functional groups on the outer surface of said shell, or Gd atoms embedded within said shell. Particular such compositions are those comprising PDA-NS, wherein said metal ions are coordinated to OH groups on the outer surface of said shell or to the N atom of the indole moiety, or said atoms are embedded within said shell. Such pharmaceutical compositions are useful for diagnostic purposes such as visualization of organs and tissues or diagnosis of tumors.

In certain embodiments, the present invention provides a pharmaceutical composition comprising nanocapsules each comprising a shell obtained upon polymerization of a compound of the general formula I, e.g., dopamine, wherein said nanocapsules further comprise, as a payload, a magnetite such as $Fe_3O_4$ or $Fe_2O_3$ encapsulated by said shell. Such pharmaceutical compositions are useful for diagnostic purposes such as visualization of organs and tissues or diagnosis of tumors.

In certain embodiments, the present invention provides a pharmaceutical composition comprising nanocapsules each comprising a shell obtained upon polymerization of a compound of the general formula I, e.g., dopamine, wherein said nanocapsules further comprise, as a payload, an anticancer agent such as cisplatin or a derivative thereof linked to the outer surface of said shell, optionally via a linker. Such pharmaceutical compositions are useful in targeted chemotherapy.

In certain embodiments, the present invention provides a pharmaceutical composition comprising nanocapsules each comprising a shell obtained upon polymerization of a compound of the general formula I, e.g., dopamine, wherein said nanocapsules further comprise, as a payload, a protein or peptide, e.g., an antibody or a fragment thereof, an enzyme, or a targeting peptide or peptidomimetic, linked to the outer surface of said shell, optionally via a linker.

In certain embodiments, the present invention provides a pharmaceutical composition comprising nanocapsules each comprising a shell obtained upon polymerization of a compound of the general formula I, wherein said nanocapsules further comprise, as one payload, Ni ions coordinated to functional groups on the outer surface of said shell, and as another payload, a His-tagged recombinant protein or peptide, e.g., an antibody such as Herceptin® which selectively binds HER2 overexpressing cancers, an antibacterial enzyme such as lysostaphin or lysosyme, or a targeting peptide or peptidomimetic coordinated to said Ni ions. Particular such compositions are those comprising PDA-NS, wherein said Ni ions are coordinated to OH groups on the outer surface of said shell or to the N atom of the indole moiety.

In certain embodiments, the present invention provides a composition comprising nanocapsules each comprising a shell obtained upon polymerization of a compound of the general formula I, wherein (i) said nanocapsules further comprise, as a payload, metal ions having antibacterial properties such as $Cu^{2+}$, $Fe^{2+}$, $Mg^{2+}$ or $Ag^{+1}$ coordinated to functional groups on the outer surface of said shell, or Cu, Fe, Mg or Ag atoms, respectively, embedded within said shell; or (ii) said nanocapsules further comprise, as one payload, Ni ions coordinated to functional groups on the outer surface of said shell, and as another payload, a His-tagged recombinant antibacterial enzyme such as lysostaphin or lysosyme coordinated to said Ni ions. Particular such compositions are those comprising PDA-NS, wherein said metal ions or Ni ions are coordinated to OH groups on the outer surface of said shell or to the N atom of the indole moiety, or said atoms are embedded within said shell. Such compositions are useful as antibacterial additives, e.g., in coating of materials such as fabrics (e.g., gauze) and food plastics, or in paints, rendering the coated materials or painted surfaces antibacterial and anti-fouling.

In certain embodiments, the present invention provides a composition comprising nanocapsules each comprising a shell obtained upon polymerization of a compound of the general formula I, wherein said nanocapsules further comprise, as a payload, Ni ions coordinated to functional groups on the outer surface of said shell or Ni atoms embedded within said shell. Particular such compositions are those comprising PDA-NS, wherein said Ni ions are coordinated to OH groups on the outer surface of said shell or to the N atom of the indole moiety. Such compositions are useful in protein purification.

In certain embodiments, the present invention provides a composition comprising nanocapsules each comprising a shell obtained upon polymerization of a compound of the general formula I, e.g., dopamine, wherein said nanocapsules further comprise, as a payload, a cerium oxide such as CeO or $CeO_2$ embedded within said shell. Such compositions are useful as catalysts in various reactions, e.g., for water splitting to $H_2$ and $O_2$, or for removal of toxic gasses, e.g., toxic combustion gasses, thus reducing air pollution, more particularly conversion of CO and NO to $CO_2$ and $NO_2$, respectively.

Considering the interfacial adhesion property of PDA coatings, in still another aspect the present invention provides an anti-bacterial or anti-fouling structure comprising a substrate having a surface and sonochemically-produced PDA nanocapsules adhered to said surface, wherein (i) Cu, or Ag ions are coordinated to OH groups on the outer surface of said shell or to the N atom of the indole moiety, or Cu or Ag atoms are embedded within said shell; or (ii) lysostaphin or lysozyme is covalently linked to the outer surface of said shell, optionally via a linker; or (iii) Ni ions are coordinated to OH groups on the outer surface of said shell or to the N atom of the indole moiety, and a His-tagged lysostaphin or lysozyme is coordinated to said Ni ions.

In certain embodiments, the substrate composing the structure of the invention includes a material selected from the group consisting of glass, a doped glass, indium tin oxide (ITO)-coated glass, silicon, a doped silicon, $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a rubber, a paper material, a fabric such as cotton, a polyolefin, a membrane, an optical fiber, a ceramic, a metalized ceramic, an alumina, an electrically-conductive material, a semiconductor, steel or a stainless steel. In other embodiments, said substrate is optically transparent to the UV and visible spectral ranges. Particular such structures are those comprising a substrate in the form of wafers, beads, microparticles, nanoparticles, quantum dots or nanotubes.

The invention will now be illustrated by the following non-limiting Examples.

EXAMPLES

Experimental

All chemicals and reagents were of analytical grade. Unless otherwise stated, all chemicals were obtained from Sigma-Aldrich (Rehovot, Israel) and used as received.

Synthesis of Fluorescent Probes.

Fluorescent probes were synthesized by solid-phase peptide synthesis, employing the common Fmoc strategy and using the Rink amide 4-methylbenzhydrylamine (MBHA) resin. Coupling was carried out in N-methyl-2-pyrrolidone (NMP) using 2-(1H-benzotriazol-1-yl)-1,1,3,3-tetramethyluronium hexafluorophosphate (HBTU) as the coupling agent. Following attachment of either Fmoc-Cys(Trt)-OH or Fmoc-Ala-OH to the resin and their coupling to O-[2-(Fmoc-amino)-ethyl]-O'-[2-(diglycolyl-amino)ethyl]ethylene glycol, the terminal Fmoc groups were removed by 30% piperidine in dimethylformamide (DMF) and the resins were washed with DMF. The N-terminals of the anchored compounds were then reacted with 4-nitrobenzo-1,2,5-oxadiazole (NBD) as a fluorescent probe in a mixture of DMF and N,N-diisopropylethylamine (DIPEA). Fluorescent probes 1 (bearing a Cys residue) and 2 (bearing an Ala residue) (see Appendix A) were cleaved from the resin using a 95:2.5:2.5 mixture of trifluoroacetic acid (TFA), triisopropylsilane, and $H_2O$, and purified to homogeneity by RP-HPLC. The pure probes were analysed using MALDI-TOF/TOF, or ESI mass spectrometry.

Preparation of PDA Capsules.

PDA capsules were prepared sonochemically as described previously (Richman et al., 2011; Skirtenko et al., 2011). In brief, a solution of dopamine hydrochloride (10-100 mg) in Tris buffer (30 ml, 100 mM, pH 8.5) was overlayered with either canola oil or n-dodecane (20 ml). The tip of a high intensity ultrasonic probe was then placed at the aqueous-organic interface and the mixture was irradiated at an acoustic power of 150 W $cm^{-2}$ (20 kHz) for 12 min while being cooled in an ice-water bath. Under these conditions, a very thin layer of PDA capsules was generated as a black suspension between the organic phase and the aqueous solution. PDA capsules were also prepared from solutions of dopamine hydrochloride (10 mg) in the presence of $Cu^{2+}$ ions. In particular, dopamine hydrochloride (DA; 10 mg at concentration of 0.3 mg/ml in Tris buffer pH 8.5) was placed in a 100 ml beaker and overlaid with 20 ml of dodecane (in some cases vegetable oil or other oils were used). $CuSO_4$ (0.84 mg/ml) was then dissolved in the 30 ml Tris buffer and added to the organic layer shortly before sonication. The tip of a high intensity ultrasonic probe was then placed at the aqueous-organic interface and the mixture was irradiated with different acoustic power (usually with 150 W $cm^{-2}$; 20 kHz) for different times (usually 6 min), while being cooled in an ice-water bath. The resulting layer containing the particles was then separated and washed-centrifuged in DDW (x3) to remove unreacted reactants.

PDA capsules generated either in the absence or presence of Cu(II) were also loaded with Nile red, as a fluorescent model for non-aqueous soluble compounds, by dissolving the dye (5 mg) directly in n-dodecane or canola oil (20 ml).

In all cases, the generated PDA capsules were precipitated by their suspension in rising ratios of acetone in water, starting from 25:75 to 100% acetone, and were then resuspended in DDW and stored.

Surface modification of PDA capsules (50 µl) was achieved by agitating them overnight in a solution of fluorescent probe 1 (0.5 ml, 2 mg/ml) in Tris or PBS (100 mM, pH 7.4-8.5). Nanocapsules incubated with probe 2 and Tris or PBS (100 mM, pH 7.4-8.5) were used as controls. The particles were washed four times with $H_2O$ and resuspended in PBS prior to FACS analysis.

Characterization of PDA Capsules.

The shape and morphology of the PDA capsules were characterized by optical-fluorescence microscopy (Apo-Tome Axiolmager.z1 microscope, Zeiss, Germany), scanning electron microscopy (SEM, FEI Quanta™ 200 FEG, Hillsboro, Oreg.), high-resolution scanning electron microscopy (HR SEM; JEOL-6700F, JEOL, Japan), high-resolution transmission electron microscopy (HR TEM; JEM 2100, JEOL, Japan), Raman spectroscopy (Micro Raman Spectroscopy System, Renishaw Invia Spectrometer system, UK) and confocal microscopy (Leica-SPE microscope, Mannheim, Germany). For the SEM analyses, a sample (5 µl) of the PDA capsules was spotted onto a stainless steel grid, followed by drying and carbon sputtering. The samples were then analyzed by SEM operated at 3 kV. For HR-TEM analyses, samples were loaded on gold grids and dried for 20 minutes. Samples were then analysed at 200 kV. The size of the nanocapsules was determined by a Malvern Zetasizer Nano ZS dynamic light scattering (DLS) system (Malvern, UK). X-ray photoelectron spectroscopy (XPS) and inductively coupled plasma (ICP) analyses were carried out with a Kratos AXIS-HS spectrometer (Manchester, UK) and ULTIMA2 (Horiba Scientific, Edison, N.J.), respectively, while thermogravimetric analysis (TGA) was performed with a Q500 (TA instruments, US) analyzer.

Cell Cultures and Conditions.

PC12 cells were routinely maintained in low-glucose Dulbecco's modified Eagle's medium (DMEM) supplemented with horse serum (10%) and fetal bovine serum (FBS; 5%), L-glutamine (2 mM), penicillin (100 U/ml), and streptomycin (100 mg/ml) in a 5% $CO_2$ atmosphere at 37° C. NIH-3T3 cells were maintained in similar conditions; however, the medium contained regular DMEM supplemented with 10% FBS. To determine the toxicity of the capsules, cells (10,000 and 20,000 cells/well for PC12 and NIH-3T3, respectively) were plated in 96-well tissue-culture plates in the medium (100 and incubated overnight to allow attachment. The medium was then replaced with 100 µl of fresh medium containing various amounts (5-12.5 mg/ml) of acetone-precipitated PDA nanoparticles generated in the absence or presence of $CuSO_4$ (0.5 and 3.3 mg/ml) and the incubation was continued at 37° C. for an additional 24 hours. Cell survival was then determined by the 3-(4,5-dimethylthiazol-2-yl)-2,5-diphenyl tetrazolium bromide (MTT) assay as described (Richman et al., 2011).

Antimicrobial Activity.

A suspension of gram-positive *Staphylococcus aureus* (10 µl, strain 1313, hospital-grade) and *Streptococcus mutans* (10 µl, strain, 700610), and gram-negative *Escherichia coli* (10 strain C600), and *Pseudomonas aeruginosa* (10 µl, strain PAO1) in Luria broth (LB) containing 30% glycerol were added to 5 ml of LB in a sterile 15 ml tube. The suspensions were then incubated at 37° C. with shaking at 200 rpm for 16 hours. After centrifugation (2700 rpm, 10 min), the cells were washed with phosphate buffered saline (PBS; pH 7.4) and resuspended at a concentration of $1 \times 10^6$ cells/ml in PBS. The cell suspension (0.8 ml) was then incubated for various time periods with PDA capsules (50 µl, 12.5 mg/ml) prepared in the absence or presence of Cu(II) (0.5 or 3.3 mg $ml^{-1}$) and the volume was completed to 1 ml with sterile PBS. Serial dilutions of lysostaphin (1.62 µg/ml; 10 µl), penicillin (10,000 units/ml) and streptomycin (10 mg/ml) were used as the positive controls. Similar bacterial solutions without the capsules served as a negative control. After incubation and shaking at 37° C., 10 µl of each sample was serially diluted in 10 fold steps in PBS and then 50 µl aliquots of the diluted solutions were spread evenly on growth agar plates (1.5% agar in LB broth) for colony counting. Plates were incubated at 37° C. overnight, photographed, and the numbers of colonies were determined manually or digitally using ImageJ software. Experiments were conducted in triplicates and repeated twice.

The antibacterial activity of PDA capsules was also determined microscopically using the live/dead fluorescent assay (BacLight, Molecular Probes) following the manufacture's protocol.

Study 1. Characterization of PDA-NS Prepared by Sonochemical Irradiation, and the Antibacterial Activity of Such Nanocapsules Containing Cu(II)

In this study, the remarkable property of DA to undergo facile oxidative polymerization was combined with the versatile sonochemical approach to prepare PDA-NS from a DA emulsion under mildly basic conditions; and the influence of Cu(II) on capsule formation, toxicity and antibacterial activity was studied. The present methodology is considerably faster than the classic emulsion approach and is the first one demonstrating "one-pot" preparation of PDA-NS with diameters of about 200 nm using a sonochemical approach.

PDA particles were sonochemically prepared in 12 min from a basic solution of DA in Tris buffer (pH 8.5) overlayered with canola oil or n-dodecane as templates. The presence of $CuSO_4$ in the DA solution considerably increased the yield of the particles even when the sonication time was reduced to only 6 min. This is consistent with recent findings that the presence of $CuSO_4$ in DA solution speeds its polymerization rate as a thin film (Bernsmann et al., 2011). The capsules were also filled with Nile red as a non-aqueous soluble fluorescent dye by dissolving it directly in n-dodecane.

Figure 1A:
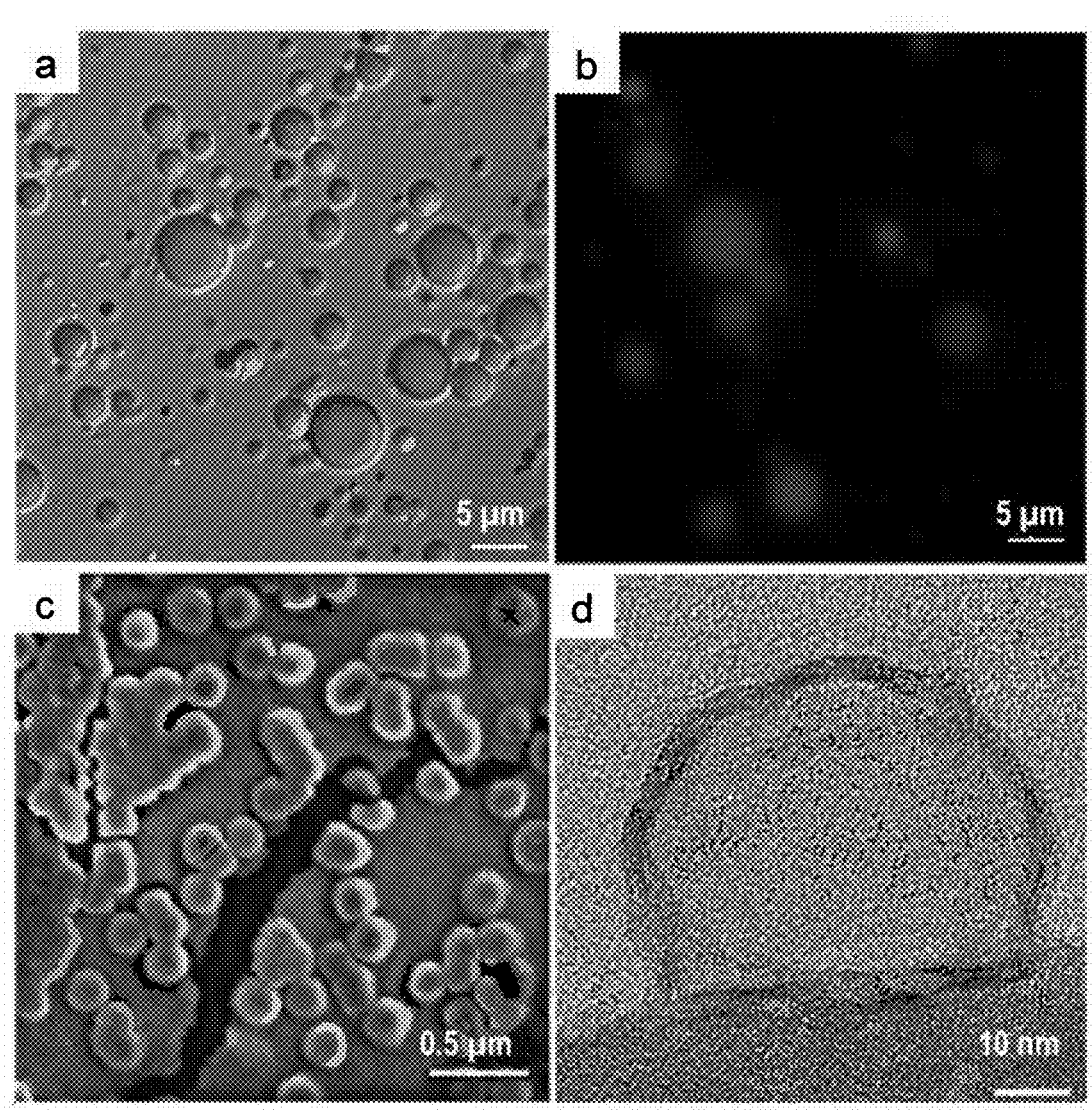
FIGS. 1A-1C show physical properties of the PDA nanocapsules (PDA-NS) prepared in the presence of 0.5 mg ml$^{-1}$ $CuSO_4$. 1A shows optical micrograph (DIC) (panel a), fluorescence-microscopy image of PDA-NS encapsulating Nile-red (panel b), SEM images of acetone-precipitated PDA-NS showing their spherical shape (panel c) and a corresponding HR-TEM image of a PDA-NS (panel d); 1B shows XPS spectra of glass surfaces coated with PDA-NS prepared in the absence (upper spectrum) or presence of 0.5 mg ml$^{-1}$ $CuSO_4$ (lower spectrum); and 1C shows UV-vis spectrum of PDA-NS prepared in the absence (gray dotted line) or presence of 0.5 mg ml$^{-1}$ $CuSO_4$ (black line).
Figure 1B:
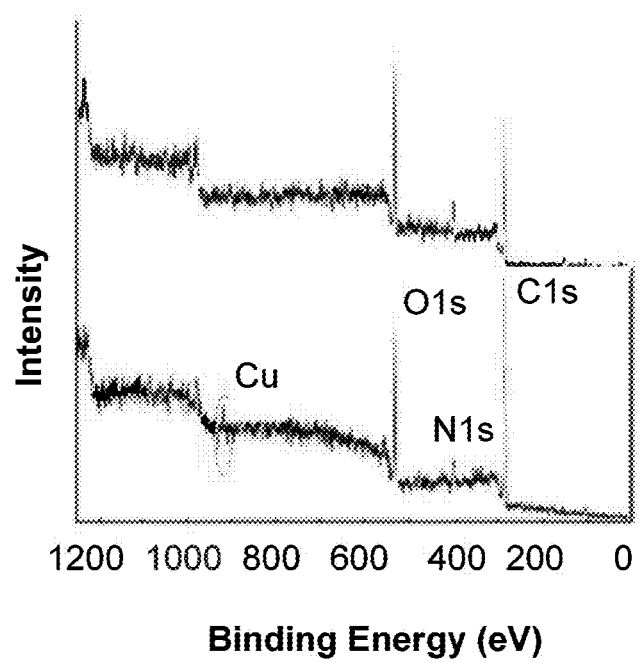
Figure 2A:
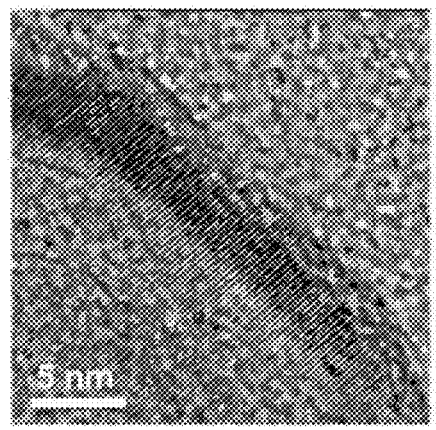
FIGS. 2A-2C show physicochemical properties of the PDA-NS prepared from 6 min irradiation of DA (0.3 mg ml$^{-1}$) and $CuSO_4$ (0.84 mg ml$^{-1}$). (2A) HR-TEM image of acetone-precipitated PDA-NS showing the thickness of about 5 nm and the crystallinity of the particles; (2B) corresponding EDS analysis of PDA-NS demonstrating the presence of C, N, O and Cu elements in PDA-NS; and (2C) XRD analysis of the PDA-NS showing crystallinity. The XRD peak at 2θ=23.4° may correspond to the d-spacing of about 3.87 Å that is consistent with π-π interactions between oligomeric PDA subunits and other π-stacked structures.
Figure 2B:
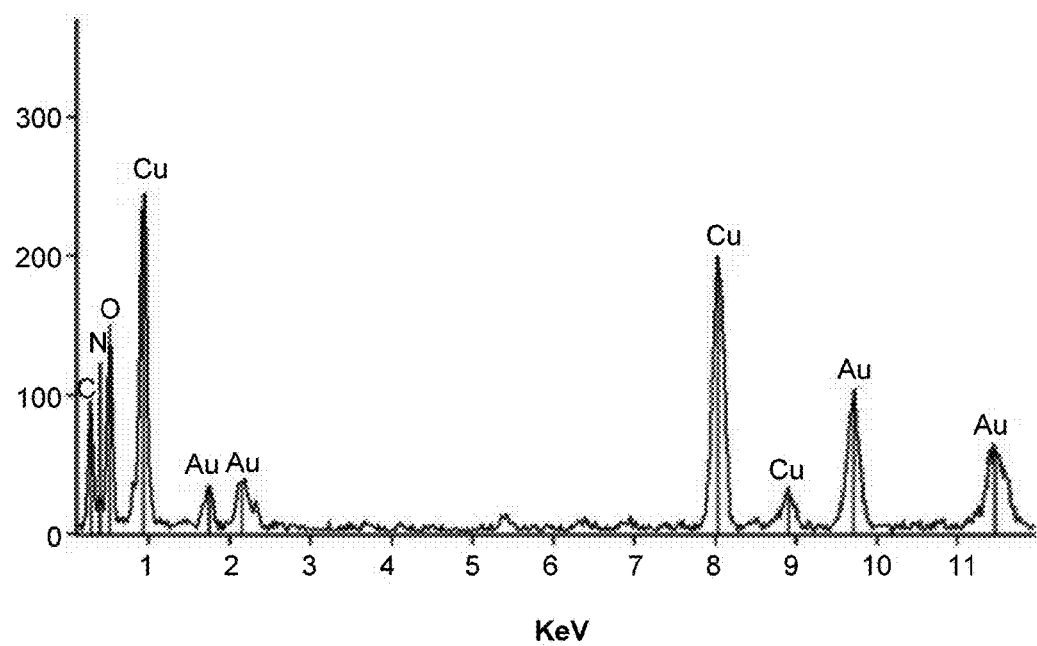
Figure 2C:
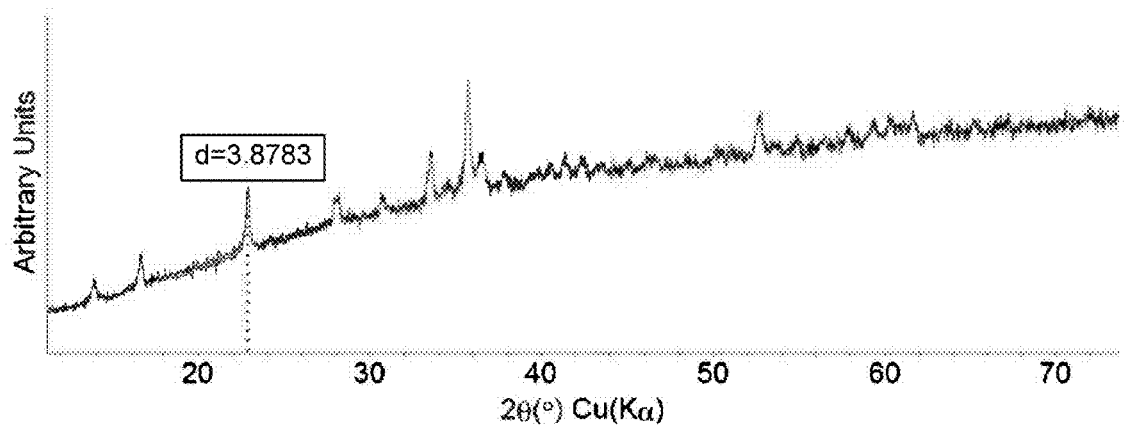

Optical microscopy images show that PDA particles prepared in the presence (FIG. 1A, panel a) or absence (data not shown) of $CuSO_4$ are relatively smooth spheres whose size varies from several hundred nanometers to about 5 micrometers. Fluorescent microscopy studies (FIG. 1A, panel b) confirm that the particles are capsules filled with n-dodecane containing Nile red. FIG. 1A, panels c and d, show SEM and TEM images of acetone precipitated PDA-NS generated in the presence of Cu(II) following 6 min of sonochemical irradiation. The dark edge and light center of the PDA particles in FIG. 1A, panel d, again confirm their capsular nature. The TEM images also suggest that the thickness of the capsules shell is about 5 nm (FIG. 2A), which is considerably thinner than previously reported values (Postma et al., 2009; Xu et al., 2011).

Figure 3A:
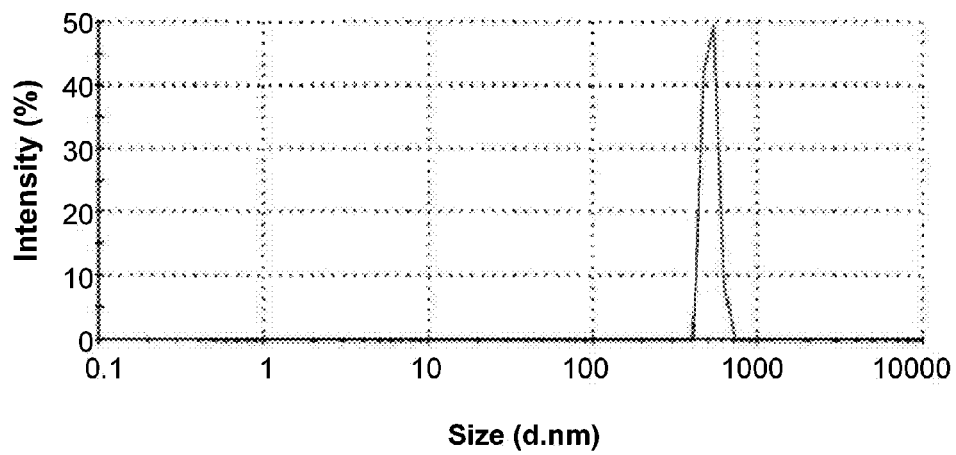
FIGS. 3A-3B show size distribution analysis of (3A) acetone precipitated PDA-NS and (3B) acetone precipitated PDA-NS prepared in the presence of 3.3 mg ml$^{-1}$ of $CuSO_4$ as recorded by DLS.
Figure 3B:
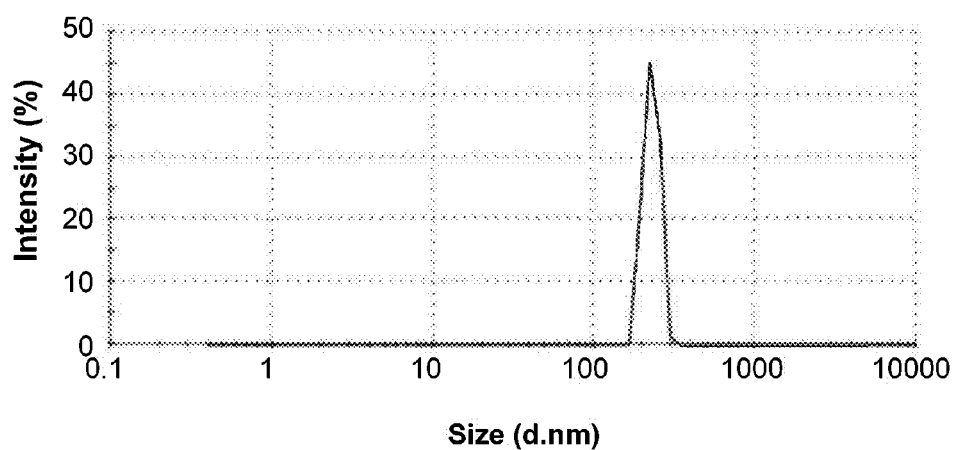
Figure 4A:
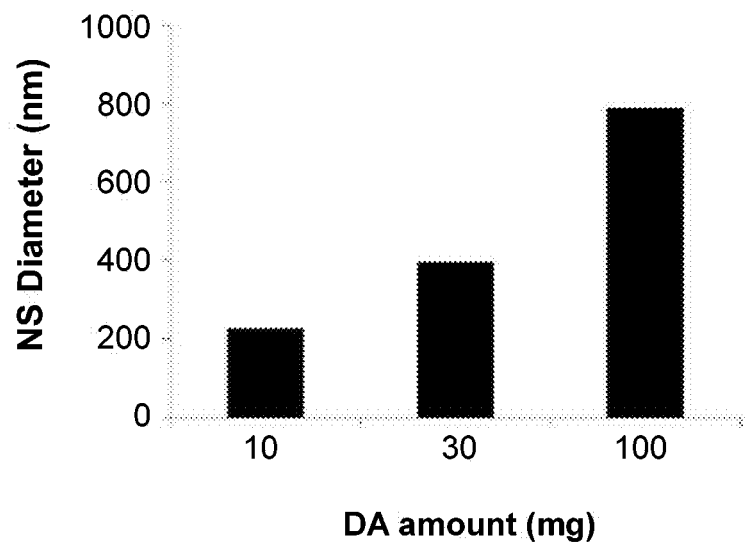
FIGS. 4A-4F show effect of DA concentration, sonication time and sonication energy on physical properties of the PDA-NS. (4A) Shows the effect of increasing DA concentration (0.3, 1, and 3.3 mg/ml) on the PDA-NS size, determined by DLS, while keeping $CuSO_4$ concentration and sonication power and time constant, and indicates a linear correlation between DA concentration and PDA-NS diameter. (4B) Shows the effect of the sonication time (6, 12 and 30 min) on the PDA-NS size, when 0.3 mg/ml DA is used, determined by DLS, indicating significant increase in the nanocapsule size while increasing sonication time. (4C) Increasing amounts of DA (0.3, 1 and 3.3 mg/ml) were sonochemically irradiated in the presence of $CuSO_4$ (4 eq.) for different periods of time and the size of the capsules was determined by DLS. (4D) Shows the effect of sonication amplitude (power) on the PDA-NS size, demonstrating that while doubling the amplitude power significantly increases the capsule size by 26 times, tripling the amplitude does not contribute to further increasing the capsule size. (4E) Representative HR-TEM image of PDA-NS prepared by 6 min irradiation of DA (3.3 mg/ml) and $CuSO_4$ (8.4 mg/ml) showing shell thickness of 12.2 nm. (4F) DLS analysis of PDA-NS prepared from DA (0.3 mg/ml) and $CuSO_4$ (0.84 mg/ml) by irradiation for 6, 12 or 30 min.
Figure 4B:
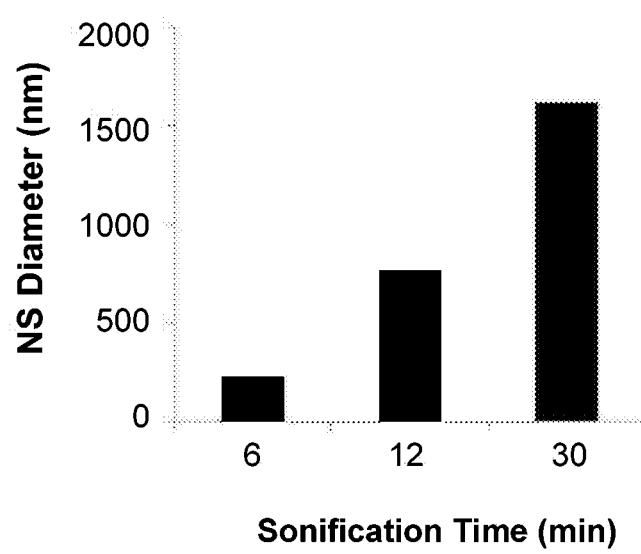
Figure 4C:
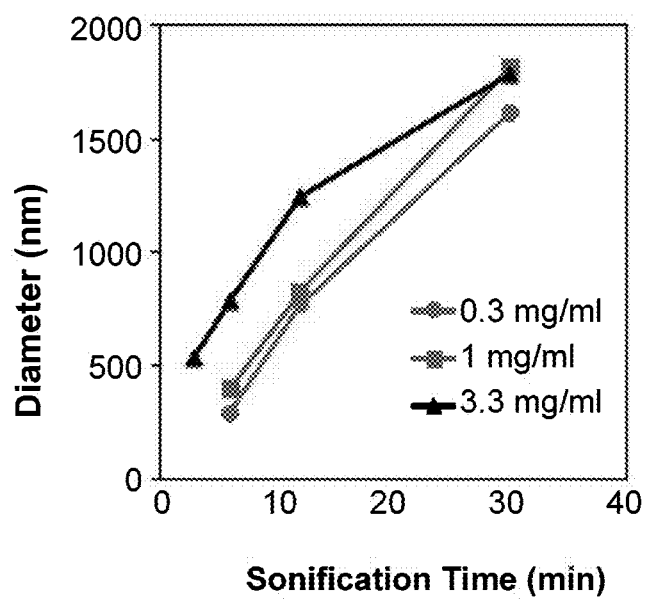
Figure 4D:
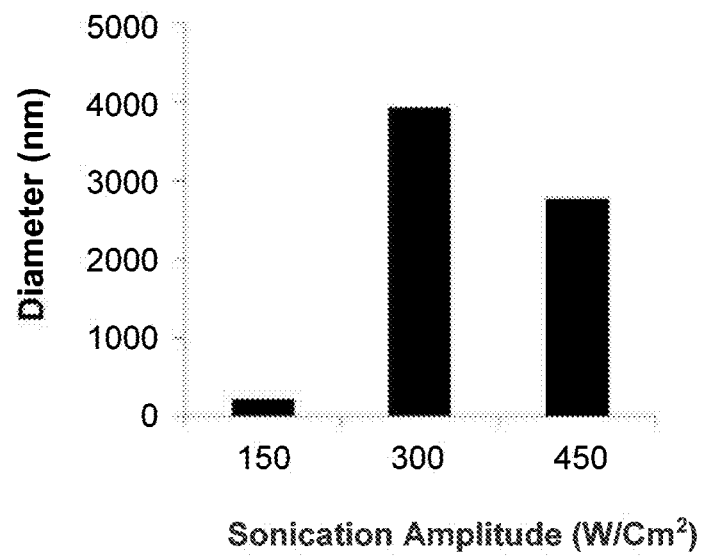
Figure 4E:
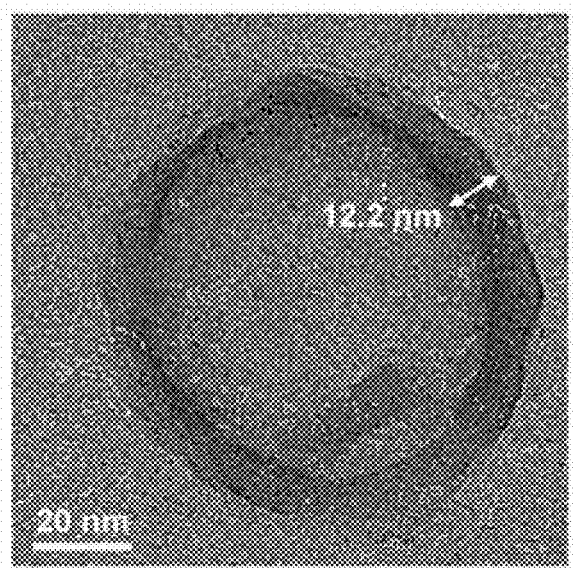
Figure 4F:
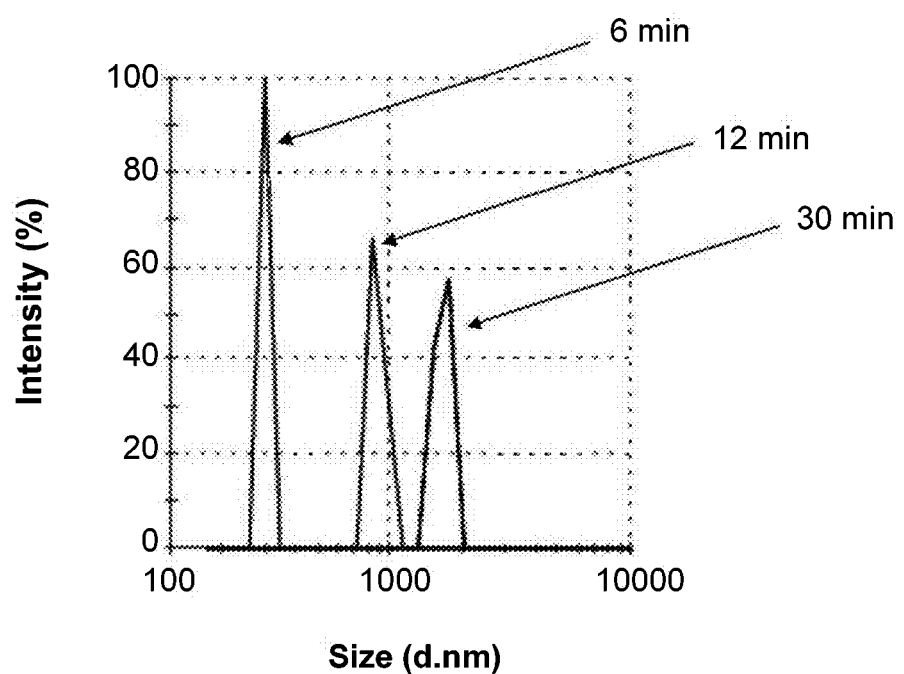

The DLS and SEM studies suggest that treating the particles with acetone leads to the precipitation of nanocapsules with diameters of 508±48 nm in the absence of $CuSO_4$. The presence of $CuSO_4$ during the preparation of the particles reduced their size to 227±25 nm possibly because of the shorter irradiation time needed for capsule preparation (FIGS. 3A-3B and FIG. 1A, panel c). These capsules are smaller than those prepared by emulsion templating (Cui et al., 2010; Yu et al., 2009; Xu et al., 2011). The narrower size distribution and smaller diameter of the acetone-treated nanocapsules most likely arise from osmotic pressure on the exteriors of the spheres during their precipitation in acetone causing the weaker and larger ones to collapse. Indeed, PDA microcapsules were demonstrated to collapse during template removal and under vacuum conditions (Cui et al., 2010; Xu et al., 2011). The DLS and SEM analyses also suggest that increasing of sonication time, DA concentration or sonication energy increase the size of the particles as well as their thickness (FIG. 4).

Figure 5:
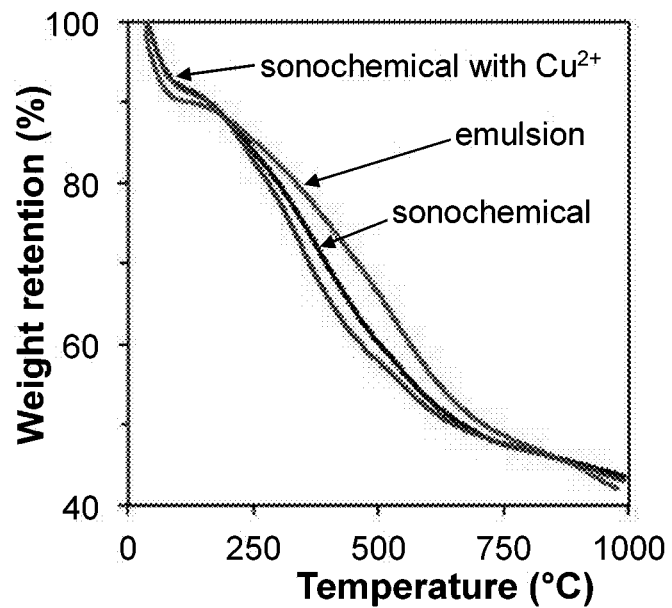
FIG. 5 shows thermogravimetric analysis of PDA-NS produced either by emulsion or sonochemical polymerization of DA (0.3 mg/ml) in the absence or presence of $Cu^{2+}$ (3.3 mg/ml).

The mechanical stability of the PDA-NS and their permeability are correlated with their size and shell thickness, which can be tuned by the template, the DA polymerization time, or the number of polymerization cycles (Dong et al., 2005). Sonochemically produced nanocapsules demonstrate excellent stability, as minimal distortion or rupture is evident in the SEM images (Ochs et al., 2011; Xu et al., 2011; Liu et al., 2011). Moreover, the thermogravimetric analysis (TGA) results show that sonochemically produced nanocapsules decompose at a similar temperature to that of capsules prepared in emulsion (Xu et al., 2011), despite their shells being considerably thinner. Furthermore, chelation of Cu(II) to the nanocapsules only slightly alters their stability (FIG. 5).

Figure 1C:
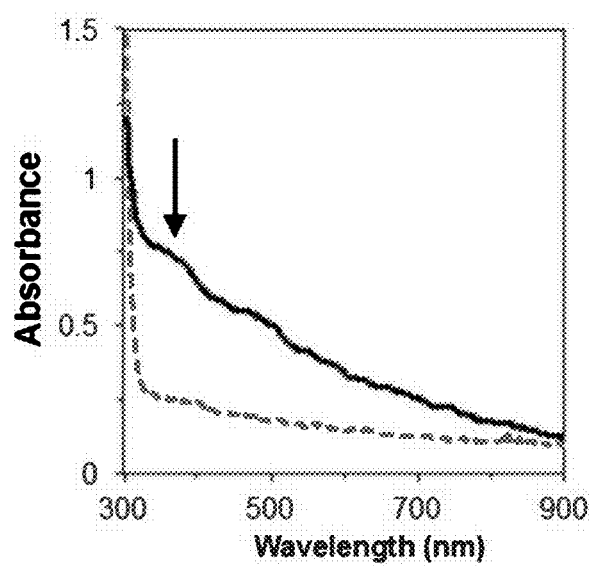

The presence of Cu(II) ions in the shells of the PDA-NS was confirmed by XPS. As shown, PDA-NS can bind Cu ions strongly and effectively remove them from aqueous solutions (Farnad et al., 2012). Moreover, Cu ions can dramatically alter the redox potential of melanin—a PDA-related biopolymer—and increase its susceptibility to react with oxygen to produce reactive oxygen species (Farmer et al., 2003). The XPS spectrum of PDA-NS prepared in the absence of $CuSO_4$ consists of C, O and N elements originating from DA, while the spectrum of those prepared in the presence of $CuSO_4$ shows the presence of Cu at 937.375 eV, corresponding to Cu(II) (FIG. 1C).

Figure 6:
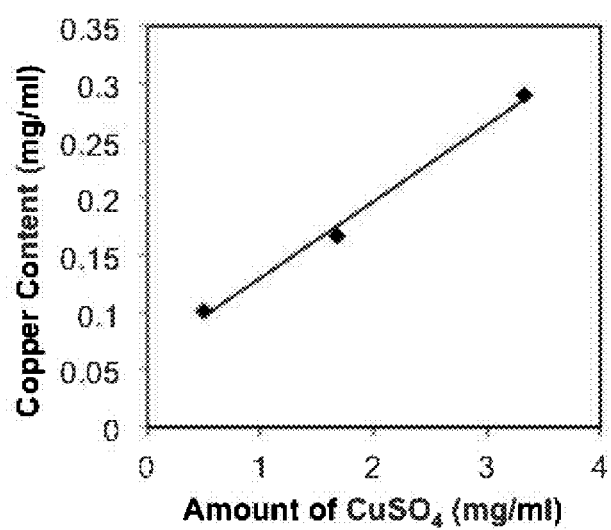
FIG. 6 shows linear correlation between different concentrations of $CuSO_4$ used for the sonochemical preparation of the PDA-NS and the Cu content of the corresponding particles as analyzed by ICP.
Figure 7A:
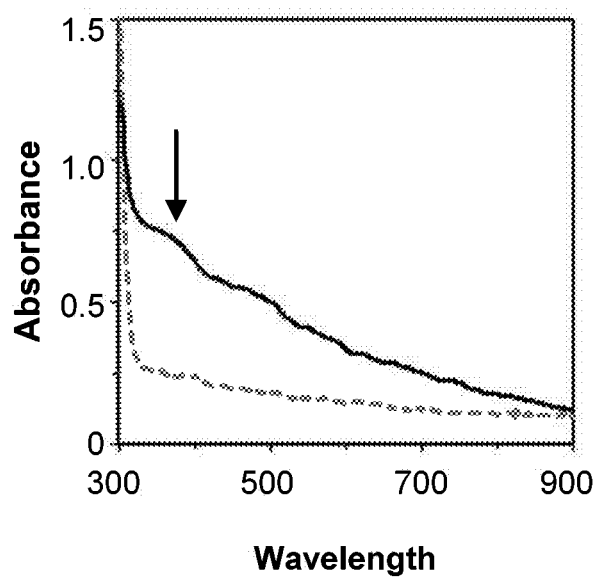
FIGS. 7A-7D show (7A) UV-vis spectrum of PDA-NS prepared in the absence (gray dotted line) or presence of 0.5 mg/ml $CuSO_4$ (black line). The UV-vis spectroscopy shows a wide peak at around 365 nm, consistent with the absorbance peak observed for PDA film produced in the presence of Cu(II) (Bernsmann et al., 2011); (7B) Raman spectra of PDA-NS prepared in the absence (red line) or presence of 0.5 mg/ml $CuSO_4$ (black line). Raman peaks at 1390 and 1580 cm$^{-1}$ corresponding to the stretching and deformation of the catechols in PDA (red line) are shifted to the lower wavenumbers upon complexation with Cu ions (black line).
Figure 7B:
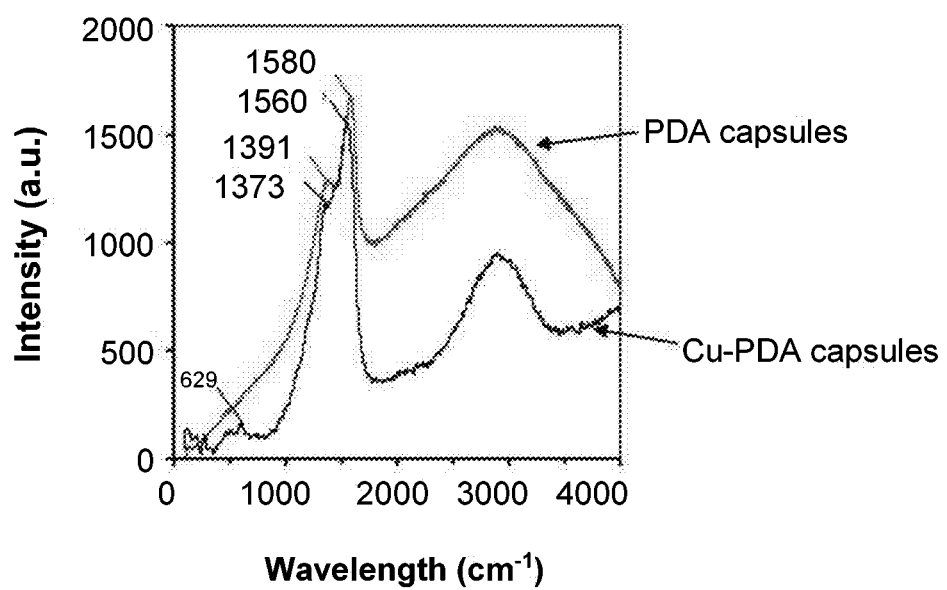
Figure 7C:
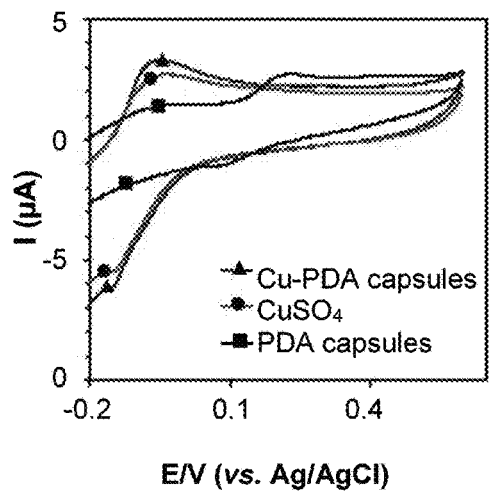
Figure 7D:
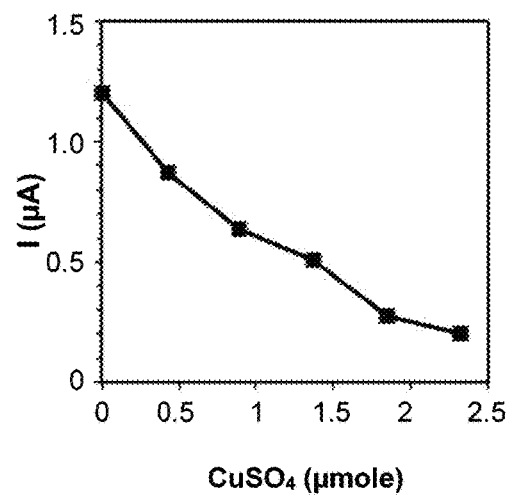

In order to further confirm that PDA-NS prepared in the presence of $CuSO_4$ chelate Cu ions and estimate their amounts in each capsule preparation, inductively coupled plasma (ICP) analysis was carried. Capsules were solubilized in dilute acidic $H_2O_2$ prior to the analysis (Szpoganicz et al., 2002). The data suggest that, in contrast to control nanocapsules prepared in the absence of $CuSO_4$, all of those made with $CuSO_4$ indeed contain Cu. Moreover, a linear correlation between the amount of $CuSO_4$ present during particle preparation and its content in the nanocapsules was observed (FIG. 6). Further evidence for chelation of Cu(II) by PDA nanocapsules is provided by UV-vis, Raman and cyclic voltammetry spectroscopy (FIG. 7).

In order to test whether the shells of the PDA-NS preserve the ability of PDA to react with different nucleophiles, acetone-treated nanocapsules were reacted with fluorescent probes containing either Cys or Ala (probes 1 and 2, respectively) at their C terminal (FIG. 8). The fluorescence of the resulting nanocapsules was then compared by fluorescence-activated cell sorting (FACS). Incubation of the nanocapsules with a fluorescent probe containing a nucleophilic thiol 1 dramatically enhanced the fluorescent signal over that obtained from naked PDA-NS, while incubation with a fluorescent probe expressing Ala 2 only slightly increased the signal (FIG. 8), suggesting that PDA shells retain the reactivity of PDA toward nucleophiles.

Since copper species are known to exhibit antibacterial activity against a wide variety of bacterial strains (Borkow and Gabbay, 2005), the antibacterial activity of PDA-NS containing increasing amount of chelated Cu(II) was determined. PDA-NS prepared with 0.3 mg/ml of DA and increasing amounts of Cu(II) show dose-dependent bactericidal activity toward *S. aureus*. Bacterial killing of 99.9% and 89.5% was observed for particles prepared in the presence of 3.3 and 0.5 mg/ml of $CuSO_4$, respectively (FIG. 9A), with most bacteria killed after 15 minutes of incubation, as shown by the live/dead assay (FIG. 9B). In control experiments, PDA-NS without chelated Cu(II) killed only 20% of the bacteria after 2.5 h incubation (FIG. 9A). Cu(II)-chelated PDA-NS were also found to be toxic to *S. mutans* and *P. aeruginosa* but not to *E. coli*. Intriguingly, the PDA-NS are not toxic to neuron-like rat phaeochromocytoma (PC12 cells, FIG. 10) and mouse fibroblast cell line (NIH-3T3; data not shown) even at the highest concentration of chelated Cu(II).

In summary, sonochemical irradiation of a DA solution in a two-phase system generates capsules in only 6 min compared with the 24 h required using the classic emulsion methodology. The capsules can be loaded with non-aqueous soluble compounds and therefore should be useful for drug delivery and imaging applications. DLS studies suggest that these capsules are significantly smaller than those generated by other methods and precipitation of the capsules with acetone generates nanocapsules with narrow size distribution. Electron microscopy analyses reveal that the shells of sonochemically-produced nanocapsules are considerably thinner than those of capsules generated by emulsion or layer-by-layer methodologies and yet thermogravimetric analysis suggests that they are as stable as capsules produced by other methods. As further demonstrated, the PDA-NS preserve the reactivity of PDA toward nucleophiles under mild conditions, which should enable facile modification of their surface for different applications such as targeted drug delivery. The PDA-NS can effectively chelate copper ions, with the amount of chelated copper correlating directly with the fast bactericidal activity of the nanocapsules.

Study 2. $Cu^{2+}$- and $Ag^{1+}$-Chelated PDA-NS Have Antibacterial Activity

In the present study, $AgNO_3$ or $CuSO_4$ were dissolved in Tris buffer (100 mM, pH 8.5) in the presence of DA (1 mg/ml), and PDA-NS were prepared in the two-phase system using the sonochemical method described above. The presence of metals on the particles was confirmed by XPS (Tables 1-2) and ICP. Metal-chelated PDA-NS were then tested for their antibacterial activity against 4 strains of bacteria including S. aureus (SA), E. Coli (EC), S. mutanus (SM) and P. aeruginosa (PA), as well as for antibiofilm activity generated by SM and PA, and the results are shown in FIG. 11 and FIG. 12, respectively.

TABLE 1

XPS analysis of PDA-NS prepared in the presence of $Ag^{1+}$

| Peak | Position BE (eV) | FWHM (eV) | Raw Area (CPS) | Atomic (conc. %) | Mass (conc. %) |
|---|---|---|---|---|---|
| O 1s | 532.625 | 1.98 | 14417.6 | 20.15 | 23.18 |
| N 1s | 400.15 | 1.652 | 1178 | 6.76 | 5.23 |
| Ag 3d | 368.75 | 1.252 | 5331.2 | 2.45 | 14.6 |
| C 1s | 285 | 1.155 | 11942.1 | 70.64 | 56.99 |

TABLE 2

XPS analysis of PDA-NS prepared in the presence of $Cu^{2+}$

| Peak | Position BE (eV) | FWHM (eV) | Raw Area (CPS) | Atomic (conc. %) | Mass (conc. %) |
|---|---|---|---|---|---|
| O 1s | 532.475 | 1.982 | 17381 | 36.6 | 43.09 |
| N 1s | 399.95 | 1.132 | 1046.4 | 3.67 | 3.78 |
| Cu 2p | 933.575 | 0.163 | 263.9 | 0.09 | 0.41 |
| C 1s | 285 | 1.503 | 9681.2 | 59.64 | 52.71 |

Study 3. Cisplatin-Conjugated PDA-NS as Potential Anticancer Treatment

In this study, the cisplatin (CP) analogue of dopamine herein designated analogue 3 (see Appendix A) was synthesized as previously described (Gandolfi and Blum, 1983) and was conjugated to PDA-NS by simple overnight incubation in Tris buffer (100 mM, pH 8.5) and acetonitrile (1:1, v:v). The presence of Pt on the particles was confirmed by XPS as described above (Table 3).

TABLE 3

XPS analysis of PDA-NS coated with the cisplatin analog.

| Peak | Position BE (eV) | FWHM (eV) | Raw Area (CPS) | Atomic (conc. %) | Mass (conc. %) |
|---|---|---|---|---|---|
| O 1s | 532.325 | 1.708 | 8731.1 | 48.32 | 52.83 |
| N 1s | 399.75 | 0.241 | 188.1 | 1.73 | 1.66 |
| C 1s | 284.95 | 1.312 | 3062.6 | 49.58 | 40.7 |
| Pt 4f | 73.35 | 0.902 | 377.5 | 0.36 | 4.81 |

In order to compare the toxicity of cisplatin-coated PDA-NS (CP-PDA-NS) to those of CP and analogue 3, cells (MCF7, PC3, PC12, THP-1 and NIH-3T3-1 cells; 20,000 cells/well) were plated in 96-well tissue culture plates in 100 μl of appropriate medium and incubated for overnight for attachment. The medium was then replaced with 0.1 μl of fresh medium containing increasing amounts (5-30 μl) of PDA-NS and CP-PDA-NS. In the case of CP and analogue 3, 10 μl of ×10 concentrated compounds were added to 90 μl medium to final concentration (12.5-200 μM) in the wells. Cells were incubated for 24 h and their viability was then determined by the MTT assay. The data suggested that while PDA-NS caused minimal toxicity to the different cells, CP-PDA-NS induced significant toxicity to all cancer cells, which was higher as compared to that of both CP and analogue 3. As further found, the toxicity of the CP-PDA-NS to non-cancerous NIH-3T3 cells was significantly lower than that to cancerous cells (FIG. 13).

In order to determine the effect of CP and its analogue on DNA binding and DNA damage, pcDNA™3.1-GFP plasmid (1 μg) was mixed with increasing concentrations of CP, analogue 3, or with PDA-NS or CP-PDA-NS in 40 μl of deionized water (DDW) containing 0.1% DMSO. DDW containing DMSO (0.1%) was used as control. The mixtures were incubated at 37° C. for 24 h and then loaded onto the 0.75% agarose gel. Electrophoresis was carried using 1×TAE buffer at 120 V. The gels were visualized and photographed under UV light (FIG. 14). The data suggested that CP-PDA-NS bind DNA in a dose-dependent manner very similar to that of analogue 3 and CP alone.

The effect of PDA-NS and CP-PDA-NS on cell cycling was determined by FACS. MCF-7 cells ($1\times10^6$) were incubated with different amounts of particles (50 and 75 μl) for 24 h. Cells treated with vehicle were used as control. The cells were then collected by trypsinisation, washed, incubated with RNase and treated with propidium iodide. The content of DNA in each sample was then measured by flow cytometry (FIG. 15). As shown, incubation of the cells with CP-PDA-NS significantly increased the G0G1 population and reduced the amount of G2M, as compared to untreated cells, suggesting that treatment with CP-PDA-NS induce apoptosis to the cells. Incubation of the cells with PDA-NS did not increase the G0G1 population, supporting our toxicity results.

Study 4. $Ni^{2+}$-Chelated PDA-NS as Carriers for His-Tagged Peptides and Enzymes In this study, nickel acetate was dissolved in Tris buffer (100 mM, pH 8.5) in the presence of DA (1 mg/ml), and PDA-NS were prepared as described above. The presence of Ni was confirmed by XPS (Table 4). Ni-chelated PDA-NS (Ni-PDA-NS) were then incubated with a peptide of the sequence β-Ala-β-Ala-His-His-His-His-His-His-amide, labeled at its N-terminus with 7-nitrobenzo-2-oxa-1,3-diazole (NBD; a fluorescent probe). Conjugation of the peptide to the particles was then accomplished by incubation of the Ni-PDA-NS with said peptide in either PBS (10 mM, pH 7.4) or Tris (100 mM, pH 8.5) for overnight at room temperature.

The ability of the Ni-PDA-NS to conjugate the His-tagged molecule was then tested using FACS and compared to that of PDA-NS without the metal. The results demonstrated that the fluorescence of the Ni-containing PDA-NS was significantly higher at either buffer than particles without Ni (FIG. 16). This study suggests that other recombinantly produced His6-tagged proteins/peptides could also be easily conjugated to these particles.

TABLE 4

XPS analysis of Ni-PDA-NS

| Peak | Position BE (eV) | FWHM (eV) | Raw Area (CPS) | Atomic (conc. %) | Mass (conc. %) |
|---|---|---|---|---|---|
| Ni 2p | 855.83 | 1.785 | 1023.4 | 0.9 | 3.6 |
| O 1s | 532.455 | 1.851 | 12867 | 56.09 | 60.89 |
| N 1s | 400.33 | 1.285 | 479.5 | 3.48 | 3.31 |
| C 1s | 285.23 | 2.077 | 3099.8 | 39.53 | 32.21 |

Study 5. $Gd^{2+}$-Chelated PDA-NS for Imaging Applications

In this study, $GdCl_2$ was dissolved in Tris buffer (100 mM, pH 8.5) in the presence of DA (1 mg/ml), and PDA-NS were prepared as described above. The presence of Gd on the PDA-NS was confirmed by XPS (Table 5), and was further verified by magnetic measurements showing that while the PDA-NS are diamagnetic, the Gd-chelated PDA-NS (Gd-PDA-NS) are ferromagnetic (FIG. 17). MRI imaging clearly demonstrated the magnetism of Gd-PDA-NS and their visibility in solution.

TABLE 5

XPS analysis of Gd-PDA-NS

| Peak | Position BE (eV) | FWMH (eV) | Raw Area (CPS) | Atomic (conc. %) | Mass (conc. %) |
|---|---|---|---|---|---|
| O 1s | 532.355 | 2.002 | 12628.9 | 59.85 | 57.64 |
| N 1s | 400.48 | 0.443 | 227.6 | 1.8 | 1.51 |
| C 1s | 285.03 | 1.501 | 2659.3 | 36.87 | 26.66 |
| Gd 4d | 142.58 | 2.589 | 891.7 | 1.49 | 14.19 |

Study 6. Preparation of Magnetic Iron Oxide-Based PDA-NS

In this study, iron oxide nanopowder (5 mg, diameter 50 nm, Sigma) were dispersed in DA solution (0.5 or 1 mg/ml) in Tris buffer (100 mM, pH 8.5), and PDA-NS were prepared as described above. The particles were characterized with TEM and magnetic measurements. The TEM analyses demonstrated a core-shell structure with $Fe_3O_4$ particles located at the core and surrounded by a PDA shell of about 6 nm thick. Magnetic measurements confirm that the PDA-NS are ferromagnetic (FIG. 18).

Study 7. CeO-Doped PDA-NS for Catalysis

Nanoparticles doped with $CeO/CeO_2$ are known to be effective catalysts in reactions that convert toxic combustion gasses such as CO and NO to less noxious $CO_2$ and $NO_2$ or $N+O_2$ (Perkas et al., 2006). Moreover, cerium nanoparticles have been reported for their potent antioxidant effect in different biological systems (Lee et al., 2013; Asati et al., 2009). In order to create PDA-NS doped with $CeO/CeO_2$ particles, $(NH_4)_2Ce(NO_3)_6$ (144 mg) was dissolved in Tris buffer in the presence of DA (1 mg/ml) and PDA-NS were prepared as described above. The presence of Ce on the particles was confirmed using ICP and found to be about 0.13 mg Ce per mg of dry PDA-NS. The activity of the Ce-PDA-NS was then tested using the tetramethylbenzene (TMB) assay and compared with that of regular PDA-NS (Asati et al., 2009). In brief, increasing amounts of the particles was added to a solution of TMB substrate (eBioscience, San Diego, Calif.) in 100 μl of DDW in a 96-well plate and shaken for 5 min at room temperature. A solution of $H_3PO_4$ (50 μl, 1 M) was the added to each well to stop the reaction, and the absorbance of each well was measured at 450 nm using a plate reader (FIG. 19). The results suggested that Ce-PDA-NS oxidize TMB very efficiently, which most likely stem from the conjugated Ce. Similar activity was also reported for polymer-coated cerium oxide nanoparticles, which was used as an oxidase mimic in ELISA application (Asati et al., 2009).

APPENDIX A

Scheme 1. A possible mechanism for dopamine oxidation to reactive polydopamine and its interaction with Cu(II) (Lee et al., 2007; Szpoganicz et al., 2002)

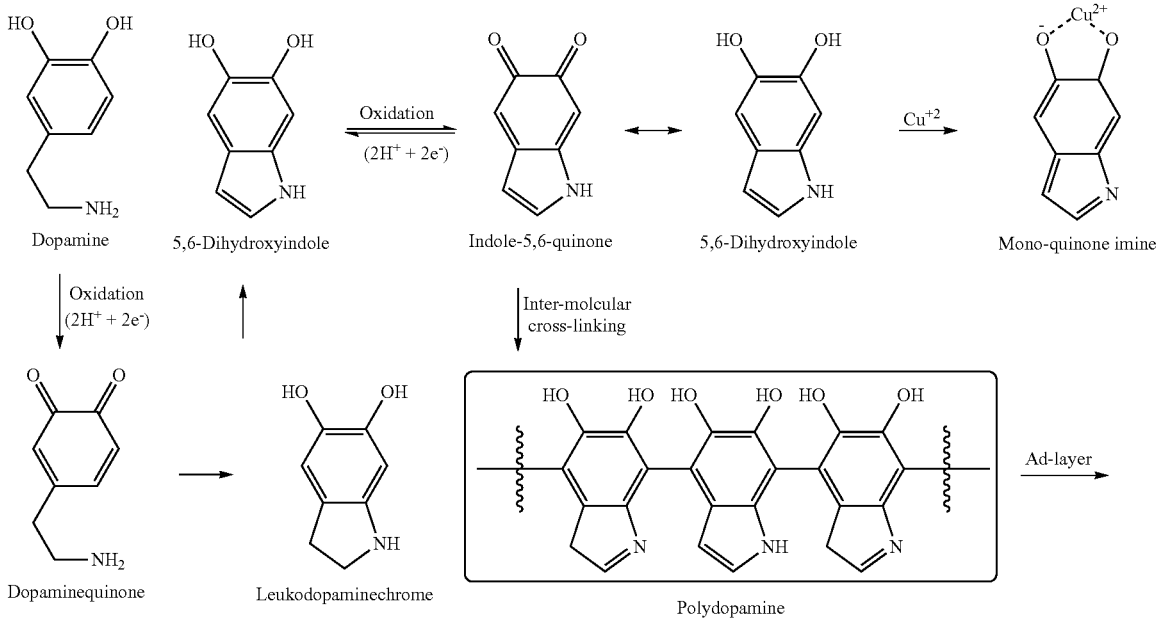

-continued

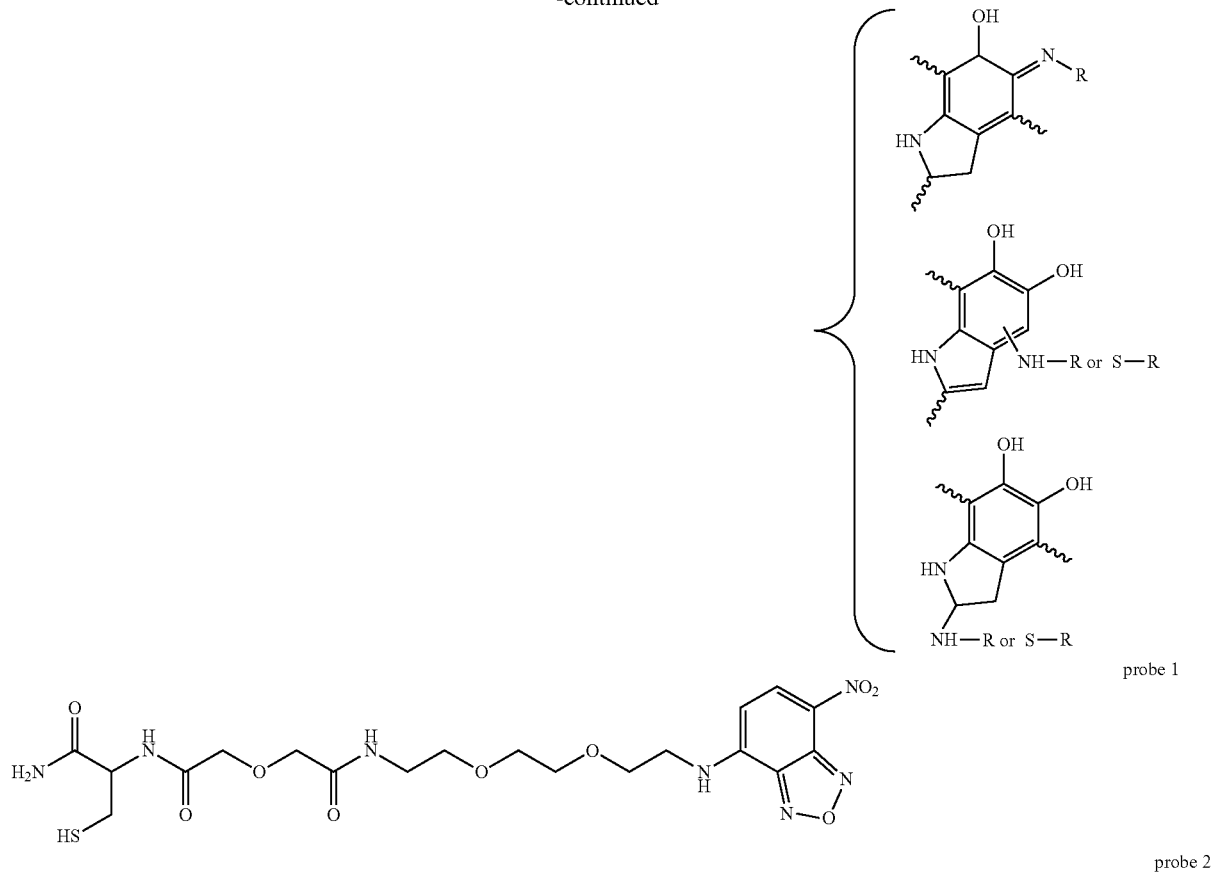

probe 1

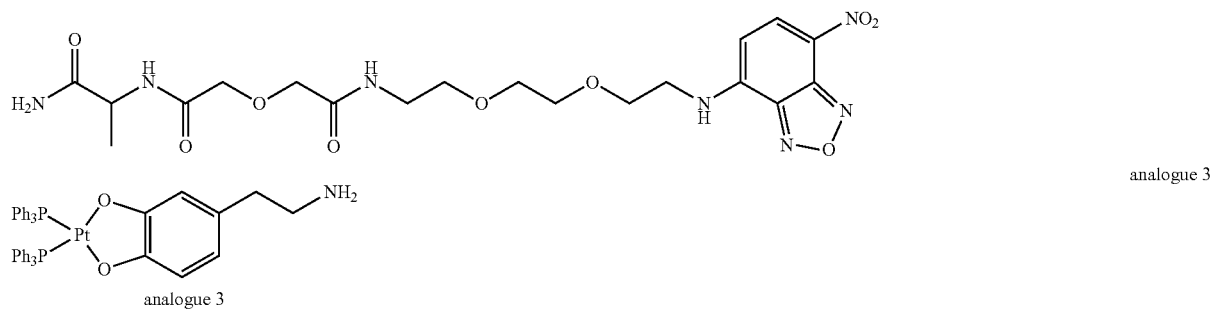

probe 2 analogue 3 analogue 3

REFERENCES

Asati, A., Santra, S., Kaittanis, C., Nath, S., Perez, J. M., *Angew Chem Int Ed Engl,* 2009, 48, 2308-2312

Avivi, S., Gedanken, A., *Biochem. 1,* 2002, 366, 705

Becker, S. C., Foster-Frey, J., Donovan, D. M., *FEMS Microbiol Lett.,* 2008, 287, 185-191

Bernsmann, F., Ball, V., Addiego, F., Ponche, A., Michel, M., Gracio, J. J., Toniazzo, V., Ruch, D., *Langmuir,* 2011

Borkow, G., Gabbay, J., *Curr. Med. Chem.,* 2005, 12, 2163

Caruso, F., Caruso, R. A., Mohwald, H., *Science,* 1998, 282, 1111

Chenglin, Y., Yiqun, Y., Ye, Z., Na, L., Xiaoya, L., Jing, L., Ming, J., *Langmuir,* 2012, 28, 9211

Chye Khoon, P., Zhilong, S., Tee Yong, L., Koon Gee, N., Wang, W., *Biomater.,* 2010, 31, 1578

Cui, J. W., Wang, Y. J., Postma, A., Hao, J. C., Hosta-Rigau, L., Caruso, F., *Adv. Func. Mater.,* 2010, 20, 1625

Cui, J., Yan, Y., Such, G. K., Liang, K., Ochs, C. J., Postma, A., Caruso, F., *Biomacromolecules,* 2012, 13, 2225

Del Duca, M., Yeager, E., Davies, M. O., Hovorka, F., I Acoust. Soc. Am., 1958, 30, 301

Dibbern, E. M., Toublan, F. J., Suslick, K. S., *J. Am. Chem. Soc.,* 2006, 128, 6540

Dong, W. F., Ferri, J. K., Adalsteinsson, T., Schonhoff, M., Sukhorukov, G. B., Mohwald, H., *Chem. Mater.,* 2005, 17, 2603

Farmer, P. J., Gidanian, S., Shahandeh, B., Di Bilio, A. J., Tohidian, N., Meyskens, F. L. Jr., *Pigment Cell Res,* 2003, 16, 273

Farnad, N., Farhadi, K., Voelcker, N., *Water Air Soil Pollut,* 2012, 223, 3535

Gandolfi, O., Blum, J., *Inorganica Chimica Acta,* 1983, 80, 103-106

Grinstaff, M. W., Suslick, K. S., *Proc. Natl. Acad. Sci. U.S.A,* 1991, 88, 7708

Kang, S. M., Ryou, M. H., Choi, J. W., Lee, H., *Chem. Mater.*, 2012, 24, 3481

Lee, H., Scherer, N. F., Messersmith, P. B., *Proc. Natl. Acad. Sci. USA*, 2006, 103, 12999

Lee, H., Dellatore, S. M., Miller, W. M., Messersmith, P. B., *Science*, 2007, 318, 426

Lee, H., Rho, J., Messersmith, P. B., *Adv. Mater.*, 2009, 21, 431

Lee, S. S., Song, W., Cho, M., Puppala, H. L., Nguyen, P., Zhu, H., Segatori, L., Colvin, V. L., *ACS Nano*, 2013, 7, 9693-9703

Lippitt, B., McCord, J. M., Fridovich, I., *J. Biol. Chem.*, 1972, 247, 4688

Liu, Q. Z., Yu, B., Ye, W. C., Zhou, F., *Macromol Biosci.*, 2011, 11, 1227-34

Ochs, C. J., Hong, T., Such, G. K., Cui, J., Postma, A., Caruso, F., *Chem. Mater.*, 2011, 23, 3141

Perkas, N., Rotter, H., Vradman, L., Landau, M. V., Gedanken A., *Langmuir*, 2006, 22, 7072-7077

Postma, A., Yan, Y., Wang, Y., Zelikin, A. N., Tjipto, E., Caruso, F., *Chem. Mater.*, 2009, 21, 3042

Ren, Y. H., Rivera, J. G., He, L. H., Kulkarni, H., Lee, D. K., Messersmith, P. B., *BMC Biotechnol.*, 2011, 11

Richman, M., Wilk, S., Skirtenko, N., Perelman, A., Rahimipour, S., *Chem. Eur. J*, 2011, 17, 11171

Shalev, T., Gopin, A., Bauer, M., Stark, R. W., Rahimipour, S., *J. Mater. Chem.*, 2012, 22, 2026

Skirtenko, N., Tzanov, T., Gedanken, A., Rahimipour, S., *Chem. Eur.* 1, 2010, 16, 562

Skirtenko, N., Richman, M., Nitzan, Y., Gedanken, A., Rahimipour, S., *Chem. Commun.*, 2011, 47, 12277

Sureshkumar, M., Siswanto, D. Y., Lee, C. K., *J. Mater. Chem.*, 2010, 20, 6948

Suslick, K. S., Grinstaff, M. W., *J. Am. Chem. Soc.*, 1990, 112, 7807

Szpoganicz, B., Gidanian, S., Kong, P., Farmer, P., *J. Inorg. Biochem.*, 2002, 89, 45

Waite, J. H., *Int. J. Adhes. Adhes.*, 1987, 7, 9

Wong, M., Suslick, K. S., *Mat. Res. Soc. Symp. Proc.*, 1995, 372, 89

Xu, H., Liu, X., Wang, D., *Chem. Mater.*, 2011, 23, 5105

Ye, Q., Zhou, F., Liu, W. M., *Chem. Soc. Rev.*, 2011, 40, 4244

Yu, B., Wang, D. A., Ye, Q., Zhou, F., Liu, W., *Chem. Commun.*, 2009, 6789

Zhang, L., Shi, J., Jiang, Z., Jiang, Y., Qiao, S., Li, J., Wang, R., Meng, R., Zhu, Y., Zheng, Y., *Green Chem.*, 2011, 13, 300

Zhang, L., Wu, J., Wang, Y., Long, Y., Zhao, N., Xu, J., *J. Am. Chem. Soc.*, 2012, 134, 9879

The invention claimed is:

1. A method for the preparation of nanocapsules each comprising a shell obtained upon polymerization of a compound of the general formula I:

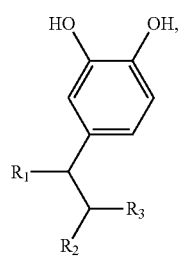

wherein
$R_1$ is H, OH, —CH$_2$OH, F or CN;
$R_2$ is H, $R_4$ or —CH$_2$—$R_4$;
$R_3$ is H, NH$_2$, OH, SH or COOH; and
$R_4$ is NH$_2$, OH or SH,
provided that $R_2$ and $R_3$ are not both H,
said shell having a thickness of less than 10 nm and greater than about 1 nm and the nanocapsules being free-standing and non-collapsed and at least 10% of the nanocapsules showing crystallinity,
said method comprising:
(i) dissolving said compound in a basic aqueous solution;
(ii) overlaying said aqueous solution with a non-aqueous solvent, thus forming a biphasic system;
(iii) applying sonication to the aqueous-non-aqueous interface of said biphasic system thereby obtaining said nanocapsules; and
(iv) isolating said nanocapsules.

2. The method of claim 1, wherein said nanocapsules each having a diameter of about 200 nm to about 1800 nm, about 300 nm to about 1000 nm, about 400 nm to about 800 nm, about 450 nm to about 650 nm, or about 500 to about 550 nm.

3. The method of claim 1, wherein (i) $R_2$ is H; and $R_3$ is NH$_2$, OH, SH or COOH; or (ii) $R_3$ is H; $R_2$ is CH$_2$—$R_4$; and $R_4$ is NH$_2$, SH or OH.

4. The method of claim 3, wherein $R_1$ and $R_2$ are H, and $R_3$ is NH$_2$ (dopamine).

5. The method of claim 4, wherein said nanocapsules have a 50% decomposition temperature (Td$_{50}$) of about 670° C. and 5% decomposition temperature (Td$_5$) of about 209° C.

6. The method of claim 1, wherein:
(i) said nanocapsules further comprise at least one payload encapsulated by said shell, said method further comprising the step of dissolving or suspending said at least one payload in said non-aqueous solvent prior to sonication; or
(ii) said nanocapsules further comprise at least one payload coordinated to functional groups on the outer surface of said shell or embedded within said shell, said functional groups being selected from the group consisting of OH, COOH, SH, NH$_2$, —N— or =N—, said method further comprising the step of dissolving said at least one payload in said aqueous solution prior to sonication; or
(iii) said nanocapsules further comprise at least one payload linked to the outer surface of said nanocapsules, optionally via a linker, said method further comprising the step of linking said at least one payload to said nanocapsules, optionally via said linker.

7. The method of claim 6, wherein said at least one payload each independently is a metal atom or an ion or oxide thereof, a diagnostic agent, a targeting agent, a therapeutic agent, or a catalyst.

8. The method of claim 7, wherein said metal is a transition metal, lanthanide, actinide, or main group element metal.

9. The method of claim 8, wherein said transition metal is Os, Ru, Fe, Pt, Pd, Ni, Ir, Rh, Co, Cu, Re, Tc, Mn, V, Nb, Ta, Hf, Zr, Cr, Mo, W, Ti, Sc, Ag, Au or Y; said lanthanide is La, Ce, Pr, Nd, Pm, Sm, Eu, Gd, Tb, Dy, Ho, Er, Tm, Yb or Lu; said actinide is Ac, Th, Pa, U, Np, Pu, Am, Cm, Bk, Cf, Es, Fm, Md, No or Lr; and said main group element metal is Zn, Ga, Ge, Al, Cd, In, Sn, Sb, Hg, Tl or Pb.

10. The method of claim 7, wherein said diagnostic agent is a dye, fluorophore, luminophore, heavy atom, quantum dot, radioactive isotope, or contrast agent; said targeting agent is a protein, peptide, amino-acid sequence, antibody or a fragment thereof, single-chain variable fragment of an antibody, nucleotide sequence, DNA sequence, RNA sequence, peptide nucleic acid sequence, carbohydrate, or steroid; and said therapeutic agent is an antibacterial agent or antibacterial enzyme, antiviral agent, antifungal agent, anticancer agent, photosensitizer, vitamin, or hormone.

11. The method of claim 10, wherein said dye is 9-diethylamino-5-benzo[α]phenoxazinone (Nile-red dye); said fluorophore is 3-mercapto-2-(14-(7-nitrobenzo[c][1,2,5]oxadiazol-4-ylamino)-5-oxo-3,9,12-trioxa-6-azatetradecanamido) propanamide; said anticancer agent is cisplatin or a derivative thereof, an anthracycline chemotherapeutic agent such as doxorubicin (adriamycin), daunorubicin, epirubicin, idarubicin and mitoxantrone, a mitotic inhibitor such as paclitaxel, a topoisomerase I inhibitor such as camptothecin, or a topoisomerase II inhibitor such as ellipticine.

12. The method of claim 7, wherein one of said at least one payload are metal ions coordinated to functional groups on the outer surface of said shell, and another one of said at least one payload is coordinated to said metal ions, said method further comprising the step of coordinating said another one of said at least one payload to said metal ions after isolation of said nanocapsules.

13. Nanocapsules obtained according to the method of claim 1, wherein said shell has a thickness of less than 10 nm and greater than about 1 nm, and the nanocapsules are free-standing and non-collapsed and at least 10% of the nanocapsules show crystallinity.

14. The nanocapsules of claim 13, each comprising a shell obtained upon polymerization of dopamine.

15. The nanocapsules of claim 14, each further comprising at least one payload each independently (i) encapsulated by said shell; or (ii) coordinated to OH groups on the outer surface of said shell or to the N atom of the indole moiety; or (iii) embedded within said shell; or (iv) linked to the outer surface of said shell, optionally via a linker; or (v) any combination of (i) to (iv).

16. The nanocapsules of claim 15, wherein metal ions are coordinated to OH groups on the outer surface of said shell or to the N atom of the indole moiety, or atoms or an oxide of said metal are embedded within said shell.

17. The nanocapsules of claim 16, wherein $Cu^{2+}$, $Fe^{2+}$, $Fe^{3+}$, $Zn^{2+}$, $Mg^{2+}$, $Mn^{2+}$, $Ag^{+1}$, $Ni^{2+}$, $Gd^{2+}$, $Ce^{2+}$ or $Ce^{4+}$ ions are coordinated to OH groups on the outer surface of said shell or to the N atom of the indole moiety, or Cu, Fe, Zn, Mg, Mn, Ag, Ni, Gd or Ce atoms or an oxide thereof are embedded within said shell.

18. The nanocapsules of claim 15, wherein said at least one payload each independently is covalently linked to the outer surface of said shell, optionally via a linker.

19. The nanocapsules of claim 18, wherein said at least one payload is covalently linked to OH groups or their oxidized form on the outer surface of said shell.

20. The nanocapsules of claim 18, wherein said linker comprises an amino acid moiety, DNA, PNA, RNA, peptide moiety, carbohydrate, or polyethylene glycol moiety.

21. The nanocapsules of claim 15, wherein said at least one payload each independently is non-covalently linked to the outer surface of said shell.

22. The nanocapsules of claim 15, wherein:
(i) a dye such as Nile-red is encapsulated by said shell; or
(ii) a magnetite such as $Fe_3O_4$ or $Fe_2O_3$ is encapsulated by said shell; or
(iii) a fluorescent probe such as 3-mercapto-2-(14-(7-nitrobenzo[c] [1,2,5]oxadiazol-4-ylamino)-5-oxo-3,9,12-trioxa-6-azatetradecanamido) propanamide is covalently linked to the outer surface of the shell; or
(iv) cisplatin or a derivative thereof is covalently linked to the outer surface of said shell; or
(v) Ni ions are coordinated to OH groups on the outer surface of said shell or to the N atom of the indole moiety, and a His-tagged protein is coordinated to said Ni ions.

23. A composition comprising nanocapsules according to claim 13.

24. The composition of claim 23, comprising nanocapsules each comprising a shell obtained upon polymerization of dopamine.

25. The composition of claim 24, further comprising a pharmaceutically acceptable carrier.

26. The composition of claim 25, wherein:
(i) $Cu^{2+}$, $Fe^{2+}$, $Mg^{2+}$ or $Ag^{+1}$ ions are coordinated to OH groups on the outer surface of said shell or to the N atom of the indole moiety, or Cu, Fe, Mg or Ag atoms are embedded within said shell, for treatment of bacterial infection; or
(ii) $Gd^{2+}$ ions are coordinated to OH groups on the outer surface of said shell or to the N atom of the indole moiety, or Gd atoms are embedded within said shell, for diagnostic purposes such as visualization of organs and tissues or diagnosis of tumors; or
(iii) a magnetite such as $Fe_3O_4$ or $Fe_2O_3$ is encapsulated by said shell, for diagnostic purposes such as visualization of organs and tissues or diagnosis of tumors; or
(iv) an anticancer agent such as cisplatin or a derivative thereof is linked to the outer surface of said shell, optionally via a linker, for use in targeted chemotherapy; or
(v) a protein or peptide such as an antibody or a fragment thereof, an enzyme, or a targeting peptide or peptidomimetic is covalently linked to the outer surface of said shell, optionally via a linker; or
(vi) Ni ions are coordinated to OH groups on the outer surface of said shell or to the N atom of the indole moiety, and a His-tagged protein or peptide such as Herceptin®, an antibacterial enzyme such as lysostaphin and lysosyme, or a targeting peptide or peptidomimetic is coordinated to said Ni ions.

27. The composition of claim 24, wherein:
(i) $Cu^{2+}$, $Fe^{2+}$, $Mg^{2+}$ or $Ag^{+1}$ ions are coordinated to OH groups on the outer surface of said shell or to the N atom of the indole moiety, or Cu, Fe, Mg or Ag atoms are embedded within said shell, for use as an antibacterial additive; or
(ii) $Ni^{2+}$ ions are coordinated to OH groups on the outer surface of said shell or to the N atom of the indole moiety, and a His-tagged an antibacterial enzyme such as lysostaphin or lysozyme is coordinated to said Ni ions, for use as an antibacterial additive; or
(iii) $Ni^{2+}$ ions are coordinated to OH groups on the outer surface of said shell or to the N atom of the indole moiety, or Ni atoms are embedded within said shell, for use in protein purification; or
(iv) a Ce oxide such as CeO or $CeO_2$ is embedded within said shell, for use as a catalyst in reactions for water splitting or for conversion of CO or NO to $CO_2$ and $NO_2$, respectively.

28. An anti-bacterial or anti-fouling structure comprising a substrate having a surface and nanocapsules according to claim 14 adhered to said surface, wherein (i) Cu, or Ag ions are coordinated to OH groups on the outer surface of said shell or to the N atom of the indole moiety, or Cu or Ag atoms are embedded within said shell; or (ii) lysostaphin or lysozyme is covalently linked to the outer surface of said shell, optionally via a linker; or (iii) Ni ions are coordinated to OH groups on the outer surface of said shell or to the N atom of the indole moiety, and a His-tagged lysostaphin or lysozyme is coordinated to said Ni ions.

29. The structure of claim 28, wherein said substrate includes a material selected from the group consisting of glass, a doped glass, indium tin oxide (ITO)-coated glass, silicon, a doped silicon, $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a rubber, a paper material, a fabric such as cotton, a polyolefin, a membrane, an optical fiber, a ceramic, a metalized ceramic, an alumina, an electrically-conductive material, a semiconductor, steel or a stainless steel; or said substrate is optically transparent to the UV and visible spectral ranges.

30. The structure of claim 29, wherein said substrate is in the form of wafers, beads, microparticles, nanoparticles, quantum dots or nanotubes.

\* \* \* \* \*